US009879066B2

(12) United States Patent
Chai et al.

(10) Patent No.: US 9,879,066 B2
(45) Date of Patent: Jan. 30, 2018

(54) INFLUENZA A H7N9 VIRUS THERAPIES

(71) Applicant: Genentech, Inc., South San Francisco, CA (US)

(72) Inventors: Ning Chai, Dublin, CA (US); Jacqueline McBride, Mountain View, CA (US); Lee Swem, Montara, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/215,738

(22) Filed: Jul. 21, 2016

(65) Prior Publication Data
US 2017/0114121 A1    Apr. 27, 2017

Related U.S. Application Data

(63) Continuation of application No. PCT/US2015/012942, filed on Jan. 26, 2015.

(60) Provisional application No. 61/931,949, filed on Jan. 27, 2014.

(51) Int. Cl.
| | | |
|---|---|---|
| *C07K 16/10* | (2006.01) | |
| *A61K 45/06* | (2006.01) | |
| *A61K 31/196* | (2006.01) | |
| *A61K 31/7012* | (2006.01) | |
| *A61K 39/395* | (2006.01) | |
| *A61K 31/215* | (2006.01) | |
| *A61K 39/00* | (2006.01) | |

(52) U.S. Cl.
CPC ........ *C07K 16/1018* (2013.01); *A61K 31/196* (2013.01); *A61K 31/215* (2013.01); *A61K 31/7012* (2013.01); *A61K 39/39575* (2013.01); *A61K 45/06* (2013.01); *A61K 2039/505* (2013.01); *A61K 2039/507* (2013.01); *C07K 2317/56* (2013.01); *C07K 2317/565* (2013.01)

(58) Field of Classification Search
CPC .............. C07K 14/005; C07K 16/1018; C07K 2317/54; C07K 2317/55; C07K 2317/56; C07K 2317/622; C07K 16/4216; C07K 2317/31; A61K 39/12; A61K 39/42; A61K 39/00
See application file for complete search history.

(56) References Cited

U.S. PATENT DOCUMENTS

| | | | | |
|---|---|---|---|---|
| 2014/0161822 A1* | 6/2014 | Xu | ........... | A61K 31/215 424/159.1 |
| 2014/0248286 A1* | 9/2014 | Xu | ........... | A61K 31/215 424/159.1 |
| 2015/0259400 A1* | 9/2015 | Xu | ........... | A61K 31/215 424/139.1 |
| 2016/0168230 A1* | 6/2016 | Xu | ........... | A61K 31/215 424/147.1 |

FOREIGN PATENT DOCUMENTS

WO    2014/078268 A2    5/2014

OTHER PUBLICATIONS

Goff et al., "Induction of Cross-Reactive Antibodies to Novel H7N9 Influenza Virus by Recombinant Newcastle Disease Virus Expressing a North American Lineage H7 Subtype Hemagglutinin" Journal of Virology 87(14):8235-8240 (Jul. 2013).
International Search Report and Written Opinion for PCT/US2015/012942.
Jensen et al., "An enzyme-linked immunosorbent assay for detection of avian influenza virus subtypes H5 and H7 antibodies" Acta Veterinaria Scandinavica 55:84 ( 2013).
Nakamura et al., "An In Vivo Human-Plasmablast Enrichment Technique Allows Rapid Identification of Therapeutic Influenza A Antibodies" Cell Host & Microbe 14:93-103 (Jul. 2013).
NP / Nucleoprotein et al: 'Rabbit Monoclonal Antibody to H7N9 Ig Type', retrieved from the Internet: URL:http://www.sinobiologicalcdn.com/reagent/11675-R707.pdf [retrieved on Mar. 26, 2015] ( Nov. 12, 2013).
'Overview of the emergence and characteristics of the avian influenza A(H7N9) virus'; Retrieved from the Internet: URL:http://www.who.int/influenza/human_animal_interface/influenza_h7n9/WHO_H7N9_review_31May13.pdf?ua=1 [retrieved on Mar. 27, 2015] ( Mar. 31, 2013).

\* cited by examiner

*Primary Examiner* — Rachel B Gill
(74) *Attorney, Agent, or Firm* — James E. Nesbitt

(57) ABSTRACT

The present invention provides anti-influenza A virus antibodies effective at binding, neutralizing, and treating influenza A H7N9 virus, compositions comprising such antibodies, and methods of using the same.

16 Claims, 10 Drawing Sheets mAb1 (Heavy chain variable)
EVQLVESGGGVVQPGRSLRLSCAASGFAFHNRAMHWVRQAPGKGLEWVALIYF
DGSKQYYADSVKGRFTISRDNSKNTVFLQMNSLRPEDTAVYYCAVPGPIFGIF
PPWSYFDHWGQGILVTVSS (SEQ ID NO:74)

mAb1 (Light chain variable)
EIVLTQSPATLSVSPGERATLSCRASQSVSHNLAWYQQKPGQAPRLLVYSAST
RATGIPARFSGSGSGTEFTLAISSLQSEDFAVYYCQHYTNYPPRLTFGGGSKV
EIK (SEQ ID NO:75)

FIG. 3A mAb1 (Heavy chain)
EVQLVESGGGVVQPGRSLRLSCAASGFAFHNRAMHWVRQAPGKGLEWVALIYF
DGSKQYYADSVKGRFTISRDNSKNTVFLQMNSLRPEDTAVYYCAVPGPIFGIF
PPWSYFDHWGQGILVTVSSASTKGPSVFPLAPSSKSTSGGTAALGCLVKDYFP
EPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO:76)

mAb1 (Light chain)
EIVLTQSPATLSVSPGERATLSCRASQSVSHNLAWYQQKPGQAPRLLVYSAST
RATGIPARFSGSGSGTEFTLAISSLQSEDFAVYYCQHYTNYPPRLTFGGGSKV
EIKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFN
RGEC (SEQ ID NO:77)

FIG. 3B mAb2 (Heavy chain variable)
QVQLVQSGAELKRPGASVKVSCKTSGYSFNNYGINWVRQAPGQGLEWMGWISA
YTGNTHYAKNFEGRVTLTTDTSTSTAYMEVRSLRSDDSAVYFCARAMIQGVVT
LYLRPGDYWGQGTLVTVSS (SEQ ID NO:78)

mAb2 (Light chain variable)
DIVMTQSPSTLSASVGDRVTITCRASQSIGNWLAWYQQKPGKAPKLLIYKVST
LESGVPSRFSGSGSGTEFTLTINSLQPDDFATYYCQRYTSNSQGFTFGQGTKL
EIK (SEQ ID NO:79)

FIG. 4A mAb2 (Heavy chain)
QVQLVQSGAELKRPGASVKVSCKTSGYSFNNYGINWVRQAPGQGLEWMGWISA
YTGNTHYAKNFEGRVTLTTDTSTSTAYMEVRSLRSDDSAVYFCARAMIQGVVT
LYLRPGDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO:80)

mAb2 (Light chain)
DIVMTQSPSTLSASVGDRVTITCRASQSIGNWLAWYQQKPGKAPKLLIYKVST
LESGVPSRFSGSGSGTEFTLTINSLQPDDFATYYCQRYTSNSQGFTFGQGTKL
EIKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFN
RGEC (SEQ ID NO:81)

FIG. 4B mAb3 (Heavy chain variable)
QVQLQESGPGLVKPSETLSLTCTVSGGLIGTGSYYWGWIRQTPGKGMEWIGSI
SYSGSTYYHPSLKSRVTISDDTSKNQLFLKLRSVTAADTAQYYCARYNWGIRY
FDFWGRGTLVTVSS (SEQ ID NO:82)

mAb3 (Light chain variable)
DIQLTQSPLSPPVTLGQPASISCRSSQSLLYTDGFTYLSWYHQRPGQSPRRLI
YKISNRDSGVPDRFSGSGSGTDFTLKISRVEAEDVGVYYCMQATHWPLTFGEG
TKVEIK (SEQ ID NO:83)

FIG. 5A mAb3 (Heavy chain)
QVQLQESGPGLVKPSETLSLTCTVSGGLIGTGSYYWGWIRQTPGKGMEWIGSI
SYSGSTYYHPSLKSRVTISDDTSKNQLFLKLRSVTAADTAQYYCARYNWGIRY
FDFWGRGTLVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNT
KVDKTRESKYGPPCPSCPAPEFLGGPSVFLFPPKPKDTLMISRTPEVTCVVVD
VSQEDPEVQFNWYVDGVEVHNAKTKPREEQFNSTYRVVSVLTVLHQDWLNGKE
YKCKVSNKGLPSSIEKTISKAKGQPREPQVYTLPPAQEEMTKNQVSLTCLVKG
FYPSDIAVEWESNGQPENNYKTTPPVLDSDGSFFLYSRLTVDKSRWQEGNVFS
CSVMHEALHNHYTQKSLSLSLGK (SEQ ID NO:84)

mAb3 (Light chain)
DIQLTQSPLSPPVTLGQPASISCRSSQSLLYTDGFTYLSWYHQRPGQSPRRLI
YKISNRDSGVPDRFSGSGSGTDFTLKISRVEAEDVGVYYCMQATHWPLTFGEG
TKVEIKPKAAPSVTLFPPSSEELQANKATLVCLISDFYPGAVTVAWKADSSPV
KAGVETTTPSKQSNNKYAASSYLSLTPEQWKSHKSYSCQVTHEGSTVEKTVAP
TECS (SEQ ID NO:85)

FIG. 5B

|   | mAb1 | mAb2 | mAb3 |
|---|---|---|---|
| HVR-H1 | GFAFHNRAMH (SEQ ID NO:56) | GYSFNNYGIN (SEQ ID NO:62) | GGLIGTGSYYWG (SEQ ID NO:68) |
| HVR-H2 | ALIYFDGSKQYYADSVKG (SEQ ID NO:57) | GWISAYTGNTHYAKNFEG (SEQ ID NO:63) | GSISYSGSTYYHPSLKS (SEQ ID NO:69) |
| HVR-H3 | AVPGPIFGIFPPWSYFDH (SEQ ID NO:58) | ARAMIQGVVTLYLRPGDYW (SEQ ID NO:64) | ARYNWGIRYFDF (SEQ ID NO:70) |
| HVR-L1 | RASQSVSHNLA (SEQ ID NO:59) | RASQSIGNWLA (SEQ ID NO:65) | RSSQSLLYTDGFTYLS (SEQ ID NO:71) |
| HVR-L2 | SASTRAT (SEQ ID NO:60) | KVSTLES (SEQ ID NO:66) | KISNRDS (SEQ ID NO:72) |
| HVR-L3 | QHYTNYPPRLT (SEQ ID NO:61) | QRYTSNSQGFT (SEQ ID NO:67) | MQATHWPLT (SEQ ID NO:73) |

FIG. 6

A/Anhui/1/2013 HA
atgaacactcaaatcctggtattcgctctgattgcgatcattccaacaaatgc
agacaaaatctgcctcggacatcatgccgtgtcaaacggaaccaaagtaaaca
cattaactgaaagaggagtggaagtcgtcaatgcaactgaaacagtggaacga
acaaacatccccaggatctgctcaaaagggaaaaggacagttgacctcggtca
atgtggactcctggggacaatcactggaccacctcaatgtgaccaattcctag
aattttcagccgatttaattattgagaggcgagaaggaagtgatgtctgttat
cctgggaaattcgtgaatgaagaagctctgaggcaattctcagagaatcagg
cggaattgacaaggaagcaatggattcacatacagtggaataagaactaatg
gagcaaccagtgcatgtaggagatcaggatcttcattctatgcagaaatgaaa
tggctcctgtcaaacacagataatgctgcattcccgcagatgactaagtcata
taaaaatacaagaaaagcccagctctaatagtatggggatccatcattccg
tatcaactgcagagcaaaccaagctatatggagtggaaacaaactggtgaca
gttgggagttctaattatcaacaatcttttgtaccgagtccaggagcgagacc
acaagttaatggtctatctggaagaattgactttcattggctaatgctaaatc
ccaatgatacagtcactttcagtttcaatggggctttcatagctccagaccgt
gcaagcttcctgagaggaaaatctatgggaatccagagtggagtacaggttga
tgccaattgtgaaggggactgctatcatagtggagggacaataataagtaact
tgccatttcagaacatagatagcaggcagttggaaaatgtccgagatatgtt
aagcaaaggagtctgctgctagcaacagggatgaagaatgttcctgagattcc
aaagggaagaggcctatttggtgctatagcgggtttcattgaaaatggatggg
aaggcctaattgatggttggtatggtttcagacaccagaatgcacagggagag
ggaactgctgcagattacaaaagcactcaatcggcaattgatcaaataacagg
aaaattaaaccggcttatagaaaaaaccaaccaacaatttgagttgatagaca
atgaattcaatgaggtagagaagcaaatcggtaatgtgataaattggaccaga
gattctataacagaagtgtggtcatacaatgctgaactcttggtagcaatgga
gaaccagcatacaattgatctggctgattcagaaatggacaaactgtacgaac
gagtgaaaagacagctgagagagaatgctgaagaagatggcactggttgcttt
gaaatatttcacaagtgtgatgatgactgtatggccagtattagaaataacac
ctatgatcacagcaaatacagggaagaggcaatgcaaaatagaatacagattg
acccagtcaaactaagcagcggctacaaagatgtgatactttggtttagcttc
ggggcatcatgtttcatacttctagccattgtaatgggccttgtcttcatatg
tgtaaagaatggaaacatgcggtgcactatttgtatataa (SEQ ID
NO:86)

FIG. 7

A/Shanghai/1/2013 HA atgaacactcaaatcctggtattcgctctgattgcgatcattccaacaaatgc
agacaaaatctgcctcggacatcatgctgtgtcaaacggaaccaaagtaaaca
cattaactgaaagaggagtggaagtcgtcaatgcaactgaaacagtggaacga
acaaacatccccaggatctgctcaaaagggaaaaggacagttgacctcggtca
atgtggactcctggggacaatcactggaccacctcaatgtgaccaattcctag
aattttcagccgatttaattattgagaggcgagaaggaagtgatgtctgttat
cctgggaaattcgtgaatgaagaagctctgaggcaaattctcagagaatcagg
cggaattgacaaggaagcaatgggattcacatacagtggaataagaactaatg
gagcaaccagttcatgtaggagatcaggatcttcattctatgcagaaatgaaa
tggctcctgtcaaacacagataatgctgcattcccgcagatgactaagtcata
taaaaatacaagaaaaaacccagctctaatagtatgggggatccatcattccg
gatcaactgcagagcaaaccaagctatatgggagtggaaacaaactggtgaca
gttgggagttctaattatcaacaatcttttgtaccgagtccgggagcgagaac
acaagttaatggtcaatctggaagaattgactttcattggctaatgctaaatc
ccaatgatacagtcactttcagtttcaatggggctttcatagctccagaccgt
gcaagcttcctgagaggaaaatctatgggaatccagagtggagtacaggttga
tgccgattgtgaaggggactgctattatagtggagggacaataataagtaact
tgccatttcagaacatagatagcagggcagttggaaaatgtccgagatatgtt
aagcaaaggagtctgctgctagcaacagggatgaagaatgttcctgagattcc
aaagggaagaggcctatttggtgctatagcgggtttcattgaaaatggatggg
aaggcctaattgatggttggtatggtttcagacaccagaatgcacagggagag
ggaactgctgcagattacaaaagcactcaatcggcaattgatcaaataacagg
aaaattaaaccggcttatagaaaaaaccaaccaacaatttgagttgatagaca
atgaattcactgaggtagagaagcaaatcggtaatgtgataaattggaccaga
gattctataacagaagtgtggtcatacaatgctgaactcttggtagcaatgga
gaaccagcatacaattgatctggctgattcagaaatggacaaactgtacgaac
gagtgaaaagacagctgagagagaatgctgaagaagatggcactggttgcttt
gaaatatttcacaagtgtgatgatgactgtatggccagcattagaaataacac
ctatgatcacagcaaatacagggaagaggcaatgcaaaatagaatacagattg
acccagtcaaactaagcagcggctacaaagatgtgatactttggtttagcttc
ggggcatcatgtttcatacttctagccattgcaatgggccttgtcttcatatg
tgtaaagaatggaaacatgcggtgcactatttgtatataa (SEQ ID
NO:87)

FIG. 8

SEQUENCE LISTING

```
<160> NUMBER OF SEQ ID NOS: 87

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gaagtagtcc ttgaccaggc ag                                            22

<210> SEQ ID NO 2
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ctcagcgtca gggtgytgct gag                                           23

<210> SEQ ID NO 3
<211> LENGTH: 18
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 3
gggtktggts gtctccac                                                      18

<210> SEQ ID NO 4
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
caggtgcagc tggtgcagtc tggggc                                             26

<210> SEQ ID NO 5
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
caggtccagc tggtgcagtc tggggc                                             26

<210> SEQ ID NO 6
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
caggtcacct tgaaggagtc tggtcc                                             26

<210> SEQ ID NO 7
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gaggtgcagc tggtggagtc tggggg                                             26

<210> SEQ ID NO 8
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
caggtgcagc tgcaggagtc gggccc                                             26
```

```
<210> SEQ ID NO 9
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gaggtgcagc tggtgcagtc tgg                                            23

<210> SEQ ID NO 10
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
caggtacagc tgcagcagtc aggtcc                                         26

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
caggtgcagc tggtgcaatc tgg                                            23

<210> SEQ ID NO 12
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
ghcatccrgw tgacccagtc tc                                             22

<210> SEQ ID NO 13
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gatrttgtga tgacycagwc tc                                             22

<210> SEQ ID NO 14
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 14
gaaatwgtrw tgacrcagtc tc                                          22

<210> SEQ ID NO 15
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gacatcgtga tgacccagtc tcc                                         23

<210> SEQ ID NO 16
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gaaacgacac tcacgcagtc tc                                          22

<210> SEQ ID NO 17
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gawrttgtgm tgacwcagtc tc                                          22

<210> SEQ ID NO 18
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
cagtctgtgy tgackcagcc rccctc                                      26

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
cagtctgccc tgactcagcc t                                           21

<210> SEQ ID NO 20
<211> LENGTH: 26
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
tcctatgagc tgacwcagsh vccckc                                           26

<210> SEQ ID NO 21
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cagcctgtgc tgactcartc vccctc                                           26

<210> SEQ ID NO 22
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
cagcctgtgc tgactcagcc aacttc                                           26

<210> SEQ ID NO 23
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
aattttatgc tgactcagcc ccac                                             24

<210> SEQ ID NO 24
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
caggctgtgg tgactcagga gccc                                             24

<210> SEQ ID NO 25
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
cagactgtgg tgacccagga gcc                                              23
```

```
<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
cagcctgtgc tgactcagcc acc                                          23

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gcagcccagg gcsgctgtgc                                              20

<210> SEQ ID NO 28
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gcacacaaca gaggcagttc cag                                          23

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cttgragctc ctcagaggag                                              20

<210> SEQ ID NO 30
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
ccaccatggg atggtcatgt atcatccttt ttctagtagc aactgcaact ggagtacatt   60
cacagg                                                             66

<210> SEQ ID NO 31
<211> LENGTH: 72
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 31
ccaccatggg atggtcatgt atcatccttt ttctagtagc aactgcaact ggagtacatt    60
cacagatcac ct                                                        72

<210> SEQ ID NO 32
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ccaccatggg atggtcatgt atcatccttt ttctagtagc aactgcaact ggagtacatt    60
cacag                                                                65

<210> SEQ ID NO 33
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
ccaccatggg atggtcatgt atcatccttt ttctagtagc aactgcaact ggagtacatt    60
cagagg                                                               66

<210> SEQ ID NO 34
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ccaccatggg atggtcatgt atcatccttt ttctagtagc aactgcaact ggagtacatt    60
cacaggtgca gctgcagg                                                  78

<210> SEQ ID NO 35
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ccaccatggg atggtcatgt atcatccttt ttctagtagc aactgcaact ggagtacatt    60
cagaggtgca                                                           70

<210> SEQ ID NO 36
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ccaccatggg atggtcatgt atcatccttt ttctagtagc aactgcaact ggagtacatt    60
cacaggtaca gc                                                        72

<210> SEQ ID NO 37
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ccaccatggg atggtcatgt atcatccttt ttctagtagc aactgcaact ggagtacatt    60
cacaggtgca                                                           70

<210> SEQ ID NO 38
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ccaccatggg atggtcatgt atcatccttt ttctagtagc aactgcaact ggagtacatt    60
cagacatcca gatgacccag tctccatcct ccctg                               95

<210> SEQ ID NO 39
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ccaccatggg atggtcatgt atcatccttt ttctagtagc aactgcaact ggagtacatt    60
cagatattgt gatgactcag tctcactctc cctgc                               95

<210> SEQ ID NO 40
<211> LENGTH: 101
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
ccaccatggg atggtcatgt atcatccttt ttctagtagc aactgcaact ggagtacatt    60
cagaaattgt gttgacacag tctccagcca ccctgtcttt g                       101

<210> SEQ ID NO 41
<211> LENGTH: 101
<212> TYPE: DNA

<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 41
ccaccatggg atggtcatgt atcatccttt ttctagtagc aactgcaact ggagtacatt    60
cagacatcgt gatgacccag tctccagact ccctggctgt g    101

<210> SEQ ID NO 42
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 42
ccaccatggg atggtcatgt atcatccttt ttctagtagc aactgcaact ggagtacatt    60
cagaaacgac actcacgcag tctccagc    88

<210> SEQ ID NO 43
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 43
ccaccatggg atggtcatgt atcatccttt ttctagtagc aactgcaact ggagtacatt    60
cagaaattgt gctgactcag tctccagact ttcg    94

<210> SEQ ID NO 44
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 44
ccaccatggg atggtcatgt atcatccttt ttctagtagc aactgcaact ggagtacatt    60
cacagtctgt gytgackcag ccrccctc    88

<210> SEQ ID NO 45
<211> LENGTH: 83
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 45
ccaccatggg atggtcatgt atcatccttt ttctagtagc aactgcaact ggagtacatt    60
cacagtctgc cctgactcag cct    83

<210> SEQ ID NO 46
<211> LENGTH: 88

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
ccaccatggg atggtcatgt atcatccttt ttctagtagc aactgcaact ggagtacatt    60
catcctatga gctgacwcag shvccckc                                       88

<210> SEQ ID NO 47
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
ccaccatggg atggtcatgt atcatccttt ttctagtagc aactgcaact ggagtacatt    60
cacagcctgt gctgactcar tcvccctc                                       88

<210> SEQ ID NO 48
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ccaccatggg atggtcatgt atcatccttt ttctagtagc aactgcaact ggagtacatt    60
cacagcctgt gctgactcag ccaacttc                                       88

<210> SEQ ID NO 49
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
ccaccatggg atggtcatgt atcatccttt ttctagtagc aactgcaact ggagtacatt    60
caaattttat gctgactcag ccccac                                         86

<210> SEQ ID NO 50
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
ccaccatggg atggtcatgt atcatccttt ttctagtagc aactgcaact ggagtacatt    60
cacaggctgt ggtgactcag gagccc                                         86

<210> SEQ ID NO 51

```
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ccaccatggg atggtcatgt atcatccttt ttctagtagc aactgcaact ggagtacatt      60
cacagactgt ggtgacccag gagcc                                           85

<210> SEQ ID NO 52
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ccaccatggg atggtcatgt atcatccttt ttctagtagc aactgcaact ggagtacatt      60
cacagcctgt gctgactcag ccacc                                           85

<210> SEQ ID NO 53
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53 gccagggggaa agaccgatg                                                 19

<210> SEQ ID NO 54
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ctgggataga agttattcag caggcacaca acagaagcag ttccagattt caactgctc      59

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
cttgragctc ctcagaggag                                                 20

<210> SEQ ID NO 56
<211> LENGTH: 10
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 56

Gly Phe Ala Phe His Asn Arg Ala Met His
1               5                   10

<210> SEQ ID NO 57
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ala Leu Ile Tyr Phe Asp Gly Ser Lys Gln Tyr Tyr Ala Asp Ser Val
1               5                   10                  15

Lys Gly

<210> SEQ ID NO 58
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Ala Val Pro Gly Pro Ile Phe Gly Ile Phe Pro Pro Trp Ser Tyr Phe
1               5                   10                  15

Asp His

<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Arg Ala Ser Gln Ser Val Ser His Asn Leu Ala
1               5                   10

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ser Ala Ser Thr Arg Ala Thr
1               5

<210> SEQ ID NO 61
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln His Tyr Thr Asn Tyr Pro Pro Arg Leu Thr
1               5                   10

<210> SEQ ID NO 62
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Tyr Ser Phe Asn Asn Tyr Gly Ile Asn
1               5                   10

<210> SEQ ID NO 63
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Trp Ile Ser Ala Tyr Thr Gly Asn Thr His Tyr Ala Lys Asn Phe
1               5                   10                  15

Glu Gly

<210> SEQ ID NO 64
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ala Arg Ala Met Ile Gln Gly Val Val Thr Leu Tyr Leu Arg Pro Gly
1               5                   10                  15

Asp Tyr Trp

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Arg Ala Ser Gln Ser Ile Gly Asn Trp Leu Ala
1               5                   10

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Lys Val Ser Thr Leu Glu Ser
1               5

<210> SEQ ID NO 67
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gln Arg Tyr Thr Ser Asn Ser Gln Gly Phe Thr
1               5                   10

<210> SEQ ID NO 68
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gly Gly Leu Ile Gly Thr Gly Ser Tyr Tyr Trp Gly
1               5                   10

<210> SEQ ID NO 69
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Ser Ile Ser Tyr Ser Gly Ser Thr Tyr Tyr His Pro Ser Leu Lys
1               5                   10                  15
Ser

<210> SEQ ID NO 70
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ala Arg Tyr Asn Trp Gly Ile Arg Tyr Phe Asp Phe
1               5                   10

<210> SEQ ID NO 71
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Arg Ser Ser Gln Ser Leu Leu Tyr Thr Asp Gly Phe Thr Tyr Leu Ser
1               5                   10                  15

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Lys Ile Ser Asn Arg Asp Ser
1               5

<210> SEQ ID NO 73
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Met Gln Ala Thr His Trp Pro Leu Thr
1               5

<210> SEQ ID NO 74
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Val Pro Gly Pro Ile Phe Gly Ile Phe Pro Pro Ser Tyr Phe
            100                 105                 110

Asp His Trp Gly Gln Gly Ile Leu Val Thr Val Ser Ser
        115                 120                 125

<210> SEQ ID NO 75
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Tyr Pro Pro
                85                  90                  95

Arg Leu Thr Phe Gly Gly Gly Ser Lys Val Glu Ile Lys
            100                 105

<210> SEQ ID NO 76
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Val Gln Leu Val Glu Ser Gly Gly Val Val Gln Pro Gly Arg
1               5                   10                  15

Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Val Pro Gly Pro Ile Phe Gly Ile Phe Pro Pro Trp Ser Tyr Phe
            100                 105                 110

Asp His Trp Gly Gln Gly Ile Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

```
Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 77
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Tyr Pro Pro
                85                  90                  95

Arg Leu Thr Phe Gly Gly Gly Ser Lys Val Glu Ile Lys Arg Thr Val
            100                 105                 110
```

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 78
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Val Gln Ser Gly Ala Glu Leu Lys Arg Pro Gly Ala
1               5                   10                  15

Ser Val Lys Val Ser Cys Lys Thr Ser Gly Tyr Ser Phe Asn Asn Tyr
            20                  25                  30

Gly Ile Asn Trp Val Arg Gln Ala Pro Gly Gln Gly Leu Glu Trp Met
        35                  40                  45

Gly Trp Ile Ser Ala Tyr Thr Gly Asn Thr His Tyr Ala Lys Asn Phe
    50                  55                  60

Glu Gly Arg Val Thr Leu Thr Thr Asp Thr Ser Thr Ser Thr Ala Tyr
65                  70                  75                  80

Met Glu Val Arg Ser Leu Arg Ser Asp Asp Ser Ala Val Tyr Phe Cys
                85                  90                  95

Ala Arg Ala Met Ile Gln Gly Val Val Thr Leu Tyr Leu Arg Pro Gly
            100                 105                 110

Asp Tyr Trp Gly Gln Gly Thr Leu Val Thr Val Ser Ser
        115                 120                 125

<210> SEQ ID NO 79
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Lys Val Ser Thr Leu Glu Ser Gly Val Pro Ser Arg Phe Ser Gly

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Arg Tyr Thr Ser Asn Ser Gln
                85                  90                  95

Gly Phe Thr Phe Gly Gln Gly Thr Lys Leu Glu Ile Lys
                100                 105

<210> SEQ ID NO 80
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 80

Gln Val Gln Leu Val Gln Ser Gly Ala Glu Leu Lys Arg Pro Gly Ala
1               5                   10                  15

Ser Val Lys Val Ser Cys Lys Thr Ser Gly Tyr Ser Phe Asn Asn Tyr
                20                  25                  30

Gly Ile Asn Trp Val Arg Gln Ala Pro Gly Gln Gly Leu Glu Trp Met
            35                  40                  45

Gly Trp Ile Ser Ala Tyr Thr Gly Asn Thr His Tyr Ala Lys Asn Phe
    50                  55                  60

Glu Gly Arg Val Thr Leu Thr Thr Asp Thr Ser Thr Ser Thr Ala Tyr
65                  70                  75                  80

Met Glu Val Arg Ser Leu Arg Ser Asp Asp Ser Ala Val Tyr Phe Cys
                85                  90                  95

Ala Arg Ala Met Ile Gln Gly Val Val Thr Leu Tyr Leu Arg Pro Gly
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Glu Glu Met Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
450                 455

<210> SEQ ID NO 81
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Lys Val Ser Thr Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Arg Tyr Thr Ser Asn Ser Gln
                85                  90                  95

Gly Phe Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

```
Val Tyr Ala Cys Glu Val Thr His Gln Gly Leu Ser Ser Pro Val Thr
            195                 200                 205
Lys Ser Phe Asn Arg Gly Glu Cys
    210                 215
```

<210> SEQ ID NO 82
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Leu Ile Gly Thr Gly
            20                  25                  30
Ser Tyr Tyr Trp Gly Trp Ile Arg Gln Thr Pro Gly Lys Gly Met Glu
        35                  40                  45
Trp Ile Gly Ser Ile Ser Tyr Ser Gly Ser Thr Tyr Tyr His Pro Ser
    50                  55                  60
Leu Lys Ser Arg Val Thr Ile Ser Asp Asp Thr Ser Lys Asn Gln Leu
65                  70                  75                  80
Phe Leu Lys Leu Arg Ser Val Thr Ala Ala Asp Thr Ala Gln Tyr Tyr
                85                  90                  95
Cys Ala Arg Tyr Asn Trp Gly Ile Arg Tyr Phe Asp Phe Trp Gly Arg
            100                 105                 110
Gly Thr Leu Val Thr Val Ser Ser
        115                 120
```

<210> SEQ ID NO 83
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Asp Ile Gln Leu Thr Gln Ser Pro Leu Ser Pro Val Thr Leu Gly
1               5                   10                  15
Gln Pro Ala Ser Ile Ser Cys Arg Ser Ser Gln Ser Leu Leu Tyr Thr
            20                  25                  30
Asp Gly Phe Thr Tyr Leu Ser Trp Tyr His Gln Arg Pro Gly Gln Ser
        35                  40                  45
Pro Arg Arg Leu Ile Tyr Lys Ile Ser Asn Arg Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Thr His Trp Pro Leu Thr Phe Gly Gly Gly Thr Lys Val Glu Ile Lys
            100                 105                 110
```

<210> SEQ ID NO 84
<211> LENGTH: 447
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 | |

Thr Leu Ser Leu Thr Cys Thr Val Ser Gly Gly Leu Ile Gly Thr Gly
                20                  25                  30

Ser Tyr Tyr Trp Gly Trp Ile Arg Gln Thr Pro Gly Lys Gly Met Glu
            35                  40                  45

Trp Ile Gly Ser Ile Ser Tyr Ser Gly Ser Thr Tyr Tyr His Pro Ser
 50                  55                  60

Leu Lys Ser Arg Val Thr Ile Ser Asp Asp Thr Ser Lys Asn Gln Leu
 65                  70                  75                  80

Phe Leu Lys Leu Arg Ser Val Thr Ala Ala Asp Thr Ala Gln Tyr Tyr
                85                  90                  95

Cys Ala Arg Tyr Asn Trp Gly Ile Arg Tyr Phe Asp Phe Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Thr Arg Glu Ser Lys Tyr Gly Pro
210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ala Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Cys Ser Val Met His Glu Ala Leu
        420                 425                 430

His Asn His Tyr Thr Gln Lys Ser Leu Ser Leu Ser Leu Gly Lys
        435                 440                 445

<210> SEQ ID NO 85
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Asp Ile Gln Leu Thr Gln Ser Pro Leu Ser Pro Val Thr Leu Gly
1               5                   10                  15

Gln Pro Ala Ser Ile Ser Cys Arg Ser Ser Gln Ser Leu Leu Tyr Thr
            20                  25                  30

Asp Gly Phe Thr Tyr Leu Ser Trp Tyr His Gln Arg Pro Gly Gln Ser
        35                  40                  45

Pro Arg Arg Leu Ile Tyr Lys Ile Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Leu Thr Phe Gly Glu Gly Thr Lys Val Glu Ile Lys
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 86
<211> LENGTH: 1683
<212> TYPE: DNA
<213> ORGANISM: Influenza A virus
<220> FEATURE:
<221> NAME/KEY: source
<223> OTHER INFORMATION: /note="Influenza A H7N9 virus A/Anhui/1/2013"

<400> SEQUENCE: 86
atgaacactc aaatcctggt attcgctctg attgcgatca ttccaacaaa tgcagacaaa      60

| | |
|---|---:|
| atctgcctcg gacatcatgc cgtgtcaaac ggaaccaaag taaacacatt aactgaaaga | 120 |
| ggagtggaag tcgtcaatgc aactgaaaca gtggaacgaa caaacatccc caggatctgc | 180 |
| tcaaaaggga aaaggacagt tgacctcggt caatgtggac tcctggggac aatcactgga | 240 |
| ccacctcaat gtgaccaatt cctagaattt tcagccgatt taattattga gaggcgagaa | 300 |
| ggaagtgatg tctgttatcc tgggaaattc gtgaatgaag aagctctgag gcaaattctc | 360 |
| agagaatcag gcggaattga caaggaagca atgggattca catacagtgg aataagaact | 420 |
| aatggagcaa ccagtgcatg taggagatca ggatcttcat tctatgcaga aatgaaatgg | 480 |
| ctcctgtcaa acacagataa tgctgcattc ccgcagatga ctaagtcata taaaaataca | 540 |
| agaaaaagcc cagctctaat agtatggggg atccatcatt ccgtatcaac tgcagagcaa | 600 |
| accaagctat atgggagtgg aaacaaactg gtgacagttg ggagttctaa ttatcaacaa | 660 |
| tcttttgtac cgagtccagg agcgagacca caagttaatg gtctatctgg aagaattgac | 720 |
| tttcattggc taatgctaaa tcccaatgat acagtcactt tcagtttcaa tggggctttc | 780 |
| atagctccag accgtgcaag cttcctgaga ggaaaatcta tgggaatcca gagtggagta | 840 |
| caggttgatg ccaattgtga aggggactgc tatcatagtg gagggacaat aataagtaac | 900 |
| ttgccatttc agaacataga tagcagggca gttggaaaat gtccgagata tgttaagcaa | 960 |
| aggagtctgc tgctagcaac agggatgaag aatgttcctg agattccaaa gggaagaggc | 1020 |
| ctatttggtg ctatagcggg tttcattgaa aatggatggg aaggcctaat tgatggttgg | 1080 |
| tatggtttca dacaccagaa tgcacaggga gagggaactg ctgcagatta caaaagcact | 1140 |
| caatcggcaa ttgatcaaat aacaggaaaa ttaaaccggc ttatagaaaa aaccaaccaa | 1200 |
| caatttgagt tgatagacaa tgaattcaat gaggtagaga agcaaatcgg taatgtgata | 1260 |
| aattggacca gagattctat aacagaagtg tggtcataca atgctgaact cttggtagca | 1320 |
| atggagaacc agcatacaat tgatctggct gattcagaaa tggacaaact gtacgaacga | 1380 |
| gtgaaaagac agctgagaga aatgctgaa gaagatggca ctggttgctt tgaaatattt | 1440 |
| cacaagtgtg atgatgactg tatggccagt attagaaata acaccatga tcacagcaaa | 1500 |
| tacagggaag aggcaatgca aaatagaata cagattgacc cagtcaaact aagcagcggc | 1560 |
| tacaaagatg tgatactttg gtttagcttc ggggcatcat gtttcatact tctagccatt | 1620 |
| gtaatgggcc ttgtcttcat atgtgtaaag aatggaaaca tgcggtgcac tatttgtata | 1680 |
| taa | 1683 |

<210> SEQ ID NO 87
<211> LENGTH: 1683
<212> TYPE: DNA
<213> ORGANISM: Influenza A virus
<220> FEATURE:
<221> NAME/KEY: source
<223> OTHER INFORMATION: /note="Influenza A H7N9 virus A/Shanghai/1/
2013"

<400> SEQUENCE: 87

| | |
|---|---:|
| atgaacactc aaatcctggt attcgctctg attgcgatca ttccaacaaa tgcagacaaa | 60 |
| atctgcctcg gacatcatgc tgtgtcaaac ggaaccaaag taaacacatt aactgaaaga | 120 |
| ggagtggaag tcgtcaatgc aactgaaaca gtggaacgaa caaacatccc caggatctgc | 180 |
| tcaaaaggga aaaggacagt tgacctcggt caatgtggac tcctggggac aatcactgga | 240 |
| ccacctcaat gtgaccaatt cctagaattt tcagccgatt taattattga gaggcgagaa | 300 |

```
ggaagtgatg tctgttatcc tgggaaattc gtgaatgaag aagctctgag gcaaattctc    360
agagaatcag gcggaattga caaggaagca atgggattca catacagtgg aataagaact    420
aatggagcaa ccagttcatg taggagatca ggatcttcat tctatgcaga aatgaaatgg    480
ctcctgtcaa acacagataa tgctgcattc ccgcagatga ctaagtcata taaaaataca    540
agaaaaaacc cagctctaat agtatggggg atccatcatt ccggatcaac tgcagagcaa    600
accaagctat atgggagtgg aaacaaactg gtgacagttg ggagttctaa ttatcaacaa    660
tcttttgtac cgagtccggg agcgagaaca caagttaatg gtcaatctgg aagaattgac    720
tttcattggc taatgctaaa tcccaatgat acagtcactt tcagtttcaa tggggctttc    780
atagctccag accgtgcaag cttcctgaga ggaaaatcta tgggaatcca gagtggagta    840
caggttgatg ccgattgtga aggggactgc tattatagtg gagggacaat aataagtaac    900
ttgccatttc agaacataga tagcagggca gttggaaaat gtccgagata tgttaagcaa    960
aggagtctgc tgctagcaac agggatgaag aatgttcctg agattccaaa gggaagaggc   1020
ctatttggtg ctatagcggg tttcattgaa aatggatggg aaggcctaat tgatggttgg   1080
tatggtttca gacaccagaa tgcacaggga gagggaactg ctgcagatta caaaagcact   1140
caatcggcaa ttgatcaaat aacaggaaaa ttaaaccggc ttatagaaaa aaccaaccaa   1200
caatttgagt tgatagacaa tgaattcact gaggtagaga agcaaatcgg taatgtgata   1260
aattggacca gagattctat aacagaagtg tggtcataca atgctgaact cttggtagca   1320
atggagaacc agcatacaat tgatctggct gattcagaaa tggacaaact gtacgaacga   1380
gtgaaaagac agctgagaga gaatgctgaa gaagatggca ctggttgctt tgaaatattt   1440
cacaagtgtg atgatgactg tatggccagc attagaaata acacctatga tcacagcaaa   1500
tacagggaag aggcaatgca aaatagaata cagattgacc cagtcaaact aagcagcggc   1560
tacaaagatg tgatactttg gtttagcttc ggggcatcat gtttcatact tctagccatt   1620
gcaatgggcc ttgtcttcat atgtgtaaag aatggaaaca tgcggtgcac tatttgtata   1680
taa                                                                 1683
```

INFLUENZA A H7N9 VIRUS THERAPIES

RELATED APPLICATIONS

This application is a continuation of International Patent Application No. PCT/US2015/012942, filed on Jan. 26, 2015, which claims priority to U.S. Provisional Patent Application No. 61/931,949, filed on Jan. 27, 2014, the disclosures of both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Jul. 19, 2016, is named P05782_US_1_SL.txt and is 51,143 bytes in size.

FIELD OF THE INVENTION

The present invention provides anti-influenza A virus antibodies effective at binding, neutralizing, and treating influenza A H7N9 virus, compositions comprising such antibodies, and methods of using the same.

BACKGROUND

Influenza A H7N9 virus is one of a subgroup of influenza viruses that normally circulate among birds, and is endemic in the Asian domestic chicken population. Until recently, this influenza virus had not been seen in humans. A novel reassortant avian influenza A H7N9 virus associated with severe human infection was first reported in early 2013 in China. (See, e.g., Gao et al. (2013) NEJM 368:1888-1897.) The initial outbreak of this avian influenza virus infection in humans during the spring of 2013 resulted in 132 confirmed cases and 44 deaths. It is believed that most of the infected individuals contracted the virus through direct contact with infected poultry.

To date, no sustained human-to-human transmission of avian influenza A H7N9 virus has been observed. However, studies using ferrets, which like humans infect one another through coughing and sneezing, showed that one influenza A H7N9 virus strain isolated from humans can transmit ferret-to-ferret through respiratory droplets.

Of significant concern is the pandemic potential of this virus. As influenza viruses constantly change, the possibility for avian H7N9 influenza virus becoming transmissible between humans, and that such transmission could result in a global pandemic cannot be excluded. If H7N9 influenza viruses acquire the ability to transmit efficiently from human to human, a worldwide outbreak may occur, as humans lack protective immune responses to these types of viruses. Therefore, a need exists for novel therapies effective at treating and preventing influenza A H7N9 virus infections in humans.

The present invention meets this need and provides other benefits for the treatment of avian influenza A H7N9 virus infection.

SUMMARY OF THE INVENTION

The present invention provides anti-hemagglutinin (anti-HA) antibodies, compositions comprising anti-hemagglutinin antibodies, and methods of using the same. The anti-hemagglutinin antibodies of the present invention are effective at neutralizing influenza A H7N9 virus; the anti-hemagglutinin antibodies of the present invention are anti-influenza A H7N9 virus antibodies, in particular anti-H7 hemagglutinin antibodies.

The instant inventors have discovered broadly neutralizing human antibodies, which bind to H7 HA protein and are effective at neutralizing influenza A H7N9 viruses. The anti-influenza A H7N9 virus antibodies of the present invention are effective at binding H7HA from, for example, influenza A H7N9 virus isolates A/Shanghai/1/2013 and A/Anhui/1/2013. Additionally, the anti-influenza A H7N9 virus antibodies of the present invention are effective at neutralizing a reassorted H7N9 influenza A virus strain, A/Shanghai/2/2013 IDCDC RG32A.

In some embodiments, an isolated anti-hemagglutinin antibody (an isolated anti-influenza A H7N9 virus antibody) of the present invention comprises three heavy chain hypervariable regions (HVR-H1, HVR-H2, and HVR-H3) and three light chain hypervariable regions (HVR-L1, HVR-L2, and HVR-L3), wherein:
  (a) HVR-H1 comprises the amino acid sequence of SEQ ID NO:56;
  (b) HVR-H2 comprises the amino acid sequence of SEQ ID NO:57;
  (c) HVR-H3 comprises the amino acid sequence of SEQ ID NO:58;
  (d) HVR-L1 comprises the amino acid sequence of SEQ ID NO:59;
  (e) HVR-L2 comprises the amino acid sequence of SEQ ID NO:60; and
  (f) HVR-L3 comprises the amino acid sequence of SEQ ID NO:61.

In some embodiments, the invention provides an isolated anti-hemagglutinin antibody (an isolated anti-influenza A H7N9 virus antibody) comprising: at least one, two, three, four, five and/or six hypervariable region (HVR) sequences, wherein:
  (a) HVR-H1 comprises the amino acid sequence of SEQ ID NO:56;
  (b) HVR-H2 comprises the amino acid sequence of SEQ ID NO:57;
  (c) HVR-H3 comprises the amino acid sequence of SEQ ID NO:58;
  (d) HVR-L1 comprises the amino acid sequence of SEQ ID NO:59;
  (e) HVR-L2 comprises the amino acid sequence of SEQ ID NO:60; and
  (f) HVR-L3 comprises the amino acid sequence of SEQ ID NO:61.

In some embodiments, the invention provides an isolated anti-hemagglutinin antibody (an isolated anti-influenza A H7N9 virus antibody) comprising three light chain hypervariable regions (HVR-L1, HVR-L2, and LVR-L3), wherein:
  (a) HVR-L1 comprises the amino acid sequence of SEQ ID NO:59;
  (b) HVR-L2 comprises the amino acid sequence of SEQ ID NO:60; and
  (c) HVR-L3 comprises the amino acid sequence of SEQ ID NO:61.

In some embodiments, the invention provides an isolated anti-hemagglutinin antibody (an isolated anti-influenza A H7N9 virus antibody) comprising three heavy chain hypervariable regions (HVR-H1, HVR-H2, and HVR-H3), wherein:
  (a) HVR-H1 comprises the amino acid sequence of SEQ ID NO:56;

(b) HVR-H2 comprises the amino acid sequence of SEQ ID NO:57; and
(c) HVR-H3 comprises the amino acid sequence of SEQ ID NO:58.

In some embodiments, the invention provides an isolated anti-hemagglutinin antibody (an isolated anti-influenza A H7N9 virus antibody) comprising: at least one, two, and/or three light chain hypervariable region (HVR) sequences, wherein:
(a) HVR-L1 comprises the amino acid sequence of SEQ ID NO:59;
(b) HVR-L2 comprises the amino acid sequence of SEQ ID NO:60; and
(c) HVR-L3 comprises the amino acid sequence of SEQ ID NO:61.

In some embodiments, the invention provides an isolated anti-hemagglutinin antibody (an isolated anti-influenza A H7N9 virus antibody) comprising: at least one, two, and/or three heavy chain hypervariable region (HVR) sequences, wherein:
(a) HVR-H1 comprises the amino acid sequence of SEQ ID NO:56;
(b) HVR-H2 comprises the amino acid sequence of SEQ ID NO:57; and
(c) HVR-H3 comprises the amino acid sequence of SEQ ID NO:58.

In some embodiments, an isolated anti-hemagglutinin antibody (an isolated anti-influenza A H7N9 virus antibody) of the present invention comprises a heavy chain variable region and a light chain variable region, wherein the heavy chain variable region comprises the amino acid sequence of SEQ ID NO:74, and the light chain variable region comprises the amino acid sequence of SEQ ID NO:75.

In some embodiments, an isolated anti-hemagglutinin antibody (an isolated anti-influenza A H7N9 virus antibody) of the present invention comprises a light chain variable region comprising the amino acid sequence of SEQ ID NO:75.

In some embodiments, an isolated anti-hemagglutinin antibody (an isolated anti-influenza A H7N9 virus antibody) of the present invention comprises a heavy chain variable region comprises the amino acid sequence of SEQ ID NOs:74.

In some embodiments, an isolated anti-hemagglutinin antibody (an isolated anti-influenza A H7N9 virus antibody) of the present invention comprises a heavy chain and a light chain, wherein the heavy chain comprises the amino acid sequence of SEQ ID NO:76, and the light chain comprises the amino acid sequence of SEQ ID NO:77.

In some embodiments, an isolated anti-hemagglutinin antibody (an isolated anti-influenza A H7N9 virus antibody) of the present invention comprises a light chain comprising the amino acid sequence of SEQ ID NO:77.

In some embodiments, an isolated anti-hemagglutinin antibody (an isolated anti-influenza A H7N9 virus antibody) of the present invention comprises a heavy chain comprising the amino acid sequence of SEQ ID NO:76.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:56;
(b) HVR-H2 comprises the amino acid sequence of SEQ ID NO:57;
(c) HVR-H3 comprises the amino acid sequence of SEQ ID NO:58;
(d) HVR-L1 comprises the amino acid sequence of SEQ ID NO:59;
(e) HVR-L2 comprises the amino acid sequence of SEQ ID NO:60; and
(f) HVR-L3 comprises the amino acid sequence of SEQ ID NO:61.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain variable region and a light chain variable region, wherein the heavy chain variable region comprises the amino acid sequence of SEQ ID NO:74, and wherein the light chain variable region comprises the amino acid sequence of SEQ ID NO:75.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain comprises the amino acid sequence of SEQ ID NO:76, and the light chain comprises the amino acid sequence of SEQ ID NO:77.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain consists of the amino acid sequence of SEQ ID NO:76, and the light chain consists of the amino acid sequence of SEQ ID NO:77.

In some embodiments, an isolated anti-hemagglutinin antibody (an isolated anti-influenza A H7N9 virus antibody) of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:62;
(b) HVR-H2 comprises the amino acid sequence of SEQ ID NO:63;
(c) HVR-H3 comprises the amino acid sequence of SEQ ID NO:64;
(d) HVR-L1 comprises the amino acid sequence of SEQ ID NO:65;
(e) HVR-L2 comprises the amino acid sequence of SEQ ID NO:66; and
(f) HVR-L3 comprises the amino acid sequence of SEQ ID NO:67.

In some embodiments, the invention provides an isolated anti-hemagglutinin antibody (an isolated anti-influenza A H7N9 virus antibody) comprising: at least one, two, three, four, five and/or six hypervariable region (HVR) sequences, wherein:
(a) HVR-H1 comprises the amino acid sequence of SEQ ID NO:62;

(b) HVR-H2 comprises the amino acid sequence of SEQ ID NO:63;
(c) HVR-H3 comprises the amino acid sequence of SEQ ID NO:64;
(d) HVR-L1 comprises the amino acid sequence of SEQ ID NO:65;
(e) HVR-L2 comprises the amino acid sequence of SEQ ID NO:66; and
(f) HVR-L3 comprises the amino acid sequence of SEQ ID NO:67.

In some embodiments, the invention provides an isolated anti-hemagglutinin antibody (an isolated anti-influenza A H7N9 virus antibody) comprising three light chain hypervariable regions (HVR-L1, HVR-L2, and LVR-L3), wherein:
(a) HVR-L1 comprises the amino acid sequence of SEQ ID NO:65;
(b) HVR-L2 comprises the amino acid sequence of SEQ ID NO:66; and
(c) HVR-L3 comprises the amino acid sequence of SEQ ID NO:67.

In some embodiments, the invention provides an isolated anti-hemagglutinin antibody (an isolated anti-influenza A H7N9 virus antibody) comprising three heavy chain hypervariable regions (HVR-H1, HVR-H2, and HVR-H3), wherein:
(a) HVR-H1 comprises the amino acid sequence of SEQ ID NO:62;
(b) HVR-H2 comprises the amino acid sequence of SEQ ID NO:63; and
(c) HVR-H3 comprises the amino acid sequence of SEQ ID NO:64.

In some embodiments, the invention provides an isolated anti-hemagglutinin antibody (an isolated anti-influenza A H7N9 virus antibody) comprising: at least one, two, and/or three light chain hypervariable region (HVR) sequences, wherein:
(a) HVR-L1 comprises the amino acid sequence of SEQ ID NO:65;
(b) HVR-L2 comprises the amino acid sequence of SEQ ID NO:66; and
(c) HVR-L3 comprises the amino acid sequence of SEQ ID NO:67.

In some embodiments, the invention provides an isolated anti-hemagglutinin antibody (an isolated anti-influenza A H7N9 virus antibody) comprising: at least one, two, and/or three heavy chain hypervariable region (HVR) sequences, wherein:
(a) HVR-H1 comprises the amino acid sequence of SEQ ID NO:62;
(b) HVR-H2 comprises the amino acid sequence of SEQ ID NO:63; and
(c) HVR-H3 comprises the amino acid sequence of SEQ ID NO:64.

In some embodiments, an isolated anti-hemagglutinin antibody (an isolated anti-influenza A H7N9 virus antibody) of the present invention comprises a heavy chain variable region and a light chain variable region, wherein the heavy chain variable region comprises the amino acid sequence of SEQ ID NO:78, and the light chain variable region comprises the amino acid sequence of SEQ ID NO:79.

In some embodiments, an isolated anti-hemagglutinin antibody (an isolated anti-influenza A H7N9 virus antibody) of the present invention comprises a light chain variable region comprising the amino acid sequence of SEQ ID NO:79.

In some embodiments, an isolated anti-hemagglutinin antibody (an isolated anti-influenza A H7N9 virus antibody) of the present invention comprises a heavy chain variable region comprises the amino acid sequence of SEQ ID NOs:78.

In some embodiments, an isolated anti-hemagglutinin antibody (an isolated anti-influenza A H7N9 virus antibody) of the present invention comprises a heavy chain and a light chain, wherein the heavy chain comprises the amino acid sequence of SEQ ID NO:80, and the light chain comprises the amino acid sequence of SEQ ID NO:81.

In some embodiments, an isolated anti-hemagglutinin antibody (an isolated anti-influenza A H7N9 virus antibody) of the present invention comprises a light chain comprising the amino acid sequence of SEQ ID NO:81.

In some embodiments, an isolated anti-hemagglutinin antibody (an isolated anti-influenza A H7N9 virus antibody) of the present invention comprises a heavy chain comprising the amino acid sequence of SEQ ID NO:80.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:62;
(b) HVR-H2 comprises the amino acid sequence of SEQ ID NO:63;
(c) HVR-H3 comprises the amino acid sequence of SEQ ID NO:64;
(d) HVR-L1 comprises the amino acid sequence of SEQ ID NO:65;
(e) HVR-L2 comprises the amino acid sequence of SEQ ID NO:66; and
(f) HVR-L3 comprises the amino acid sequence of SEQ ID NO:67.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain variable region and a light chain variable region, wherein the heavy chain variable region comprises the amino acid sequence of SEQ ID NO:78, and the light chain variable region comprises the amino acid sequence of SEQ ID NO:79.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain comprises the amino acid sequence of SEQ ID NO:80, and the light chain comprises the amino acid sequence of SEQ ID NO:81.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain consists of the amino acid sequence of SEQ ID NO:80, and the light chain consists of the amino acid sequence of SEQ ID NO:81.

In some embodiments, an isolated anti-hemagglutinin antibody (an isolated anti-influenza A H7N9 virus antibody) of the present invention comprises three heavy chain hypervariable regions (HVR-H1, HVR-H2, and HVR-H3) and three light chain hypervariable regions (HVR-L1, HVR-L2, and HVR-L3), wherein:
 (a) HVR-H1 comprises the amino acid sequence of SEQ ID NO:68;
 (b) HVR-H2 comprises the amino acid sequence of SEQ ID NO:69;
 (c) HVR-H3 comprises the amino acid sequence of SEQ ID NO:70;
 (d) HVR-L1 comprises the amino acid sequence of SEQ ID NO:71;
 (e) HVR-L2 comprises the amino acid sequence of SEQ ID NO:72; and
 (f) HVR-L3 comprises the amino acid sequence of SEQ ID NO:73.

In some embodiments, the invention provides an isolated anti-hemagglutinin antibody (an isolated anti-influenza A H7N9 virus antibody) comprising: at least one, two, three, four, five and/or six hypervariable region (HVR) sequences, wherein:
 (a) HVR-H1 comprises the amino acid sequence of SEQ ID NO:68;
 (b) HVR-H2 comprises the amino acid sequence of SEQ ID NO:69;
 (c) HVR-H3 comprises the amino acid sequence of SEQ ID NO:70;
 (d) HVR-L1 comprises the amino acid sequence of SEQ ID NO:71;
 (e) HVR-L2 comprises the amino acid sequence of SEQ ID NO:72; and
 (f) HVR-L3 comprises the amino acid sequence of SEQ ID NO:73.

In some embodiments, the invention provides an isolated anti-hemagglutinin antibody (an isolated anti-influenza A H7N9 virus antibody) comprising three light chain hypervariable regions (HVR-L1, HVR-L2, and LVR-L3), wherein:
 (a) HVR-L1 comprises the amino acid sequence of SEQ ID NO:71;
 (b) HVR-L2 comprises the amino acid sequence of SEQ ID NO:72; and
 (c) HVR-L3 comprises the amino acid sequence of SEQ ID NO:73.

In some embodiments, the invention provides an isolated anti-hemagglutinin antibody (an isolated anti-influenza A H7N9 virus antibody) comprising three heavy chain hypervariable regions (HVR-H1, HVR-H2, and HVR-H3), wherein:
 (a) HVR-H1 comprises the amino acid sequence of SEQ ID NO:68;
 (b) HVR-H2 comprises the amino acid sequence of SEQ ID NO:69; and
 (c) HVR-H3 comprises the amino acid sequence of SEQ ID NO:70.

In some embodiments, the invention provides an isolated anti-hemagglutinin antibody (an isolated anti-influenza A H7N9 virus antibody) comprising: at least one, two, and/or three light chain hypervariable region (HVR) sequences, wherein:
 (a) HVR-L1 comprises the amino acid sequence of SEQ ID NO:71;
 (b) HVR-L2 comprises the amino acid sequence of SEQ ID NO:72; and
 (c) HVR-L3 comprises the amino acid sequence of SEQ ID NO:73.

In some embodiments, the invention provides an isolated anti-hemagglutinin antibody (an isolated anti-influenza A H7N9 virus antibody) comprising: at least one, two, and/or three heavy chain hypervariable region (HVR) sequences, wherein:
 (a) HVR-H1 comprises the amino acid sequence of SEQ ID NO:68;
 (b) HVR-H2 comprises the amino acid sequence of SEQ ID NO:69; and
 (c) HVR-H3 comprises the amino acid sequence of SEQ ID NO:70.

In some embodiments, an isolated anti-hemagglutinin antibody (an isolated anti-influenza A H7N9 virus antibody) of the present invention comprises a heavy chain variable region and a light chain variable region, wherein the heavy chain variable region comprises the amino acid sequence of SEQ ID NO:82, and the light chain variable region comprises the amino acid sequence of SEQ ID NO:83.

In some embodiments, an isolated anti-hemagglutinin antibody (an isolated anti-influenza A H7N9 virus antibody) of the present invention comprises a light chain variable region comprising the amino acid sequence of SEQ ID NO:83.

In some embodiments, an isolated anti-hemagglutinin antibody (an isolated anti-influenza A H7N9 virus antibody) of the present invention comprises a heavy chain variable region comprises the amino acid sequence of SEQ ID NOs:82.

In some embodiments, an isolated anti-hemagglutinin antibody (an isolated anti-influenza A H7N9 virus antibody) of the present invention comprises a heavy chain and a light chain, wherein the heavy chain comprises the amino acid sequence of SEQ ID NO:84, and the light chain comprises the amino acid sequence of SEQ ID NO:85.

In some embodiments, an isolated anti-hemagglutinin antibody (an isolated anti-influenza A H7N9 virus antibody) of the present invention comprises a light chain comprising the amino acid sequence of SEQ ID NO:85.

In some embodiments, an isolated anti-hemagglutinin antibody (an isolated anti-influenza A H7N9 virus antibody) of the present invention comprises a heavy chain comprising the amino acid sequence of SEQ ID NO:84.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
 (a) HVR-H1 comprises the amino acid sequence of SEQ ID NO:68;
 (b) HVR-H2 comprises the amino acid sequence of SEQ ID NO:69;
 (c) HVR-H3 comprises the amino acid sequence of SEQ ID NO:70;
 (d) HVR-L1 comprises the amino acid sequence of SEQ ID NO:71;
 (e) HVR-L2 comprises the amino acid sequence of SEQ ID NO:72; and
 (f) HVR-L3 comprises the amino acid sequence of SEQ ID NO:73.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain variable region and a light chain variable region, wherein the heavy chain variable region comprises the amino acid sequence of SEQ ID NO:82, and the light chain variable region comprises the amino acid sequence of SEQ ID NO:83.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain comprises the amino acid sequence of SEQ ID NO:84, and the light chain comprises the amino acid sequence of SEQ ID NO:85.

In some embodiments, the present invention provides a method for preventing, treating, or neutralizing influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain consists of the amino acid sequence of SEQ ID NO:84, and the light chain consists of the amino acid sequence of SEQ ID NO:85.

The invention also provides isolated nucleic acids encoding an anti-influenza A H7N9 virus antibody of the present invention. The invention also provides vectors comprising a nucleic acid encoding an anti-influenza A H7N9 virus antibody of the present invention. The invention also provides host cells comprising a nucleic acid or a vector of the present invention. A vector can be of any type, for example, a recombinant vector such as an expression vector. Any of a variety of host cells can be used. In one embodiment, a host cell is a prokaryotic cell, for example, *E. coli*. In another embodiment, a host cell is a eukaryotic cell, for example, a mammalian cell, such as a Chinese Hamster Ovary (CHO) cell.

The invention further provides a method of producing an anti-influenza A H7N9 virus antibody of the present invention. For example, the invention provides methods for making an anti-influenza A H7N9 virus antibody (which, as defined herein, includes full length antibody and fragments thereof), the method comprising expressing in a suitable host cell a recombinant vector of the invention encoding the anti-influenza A H7N9 virus antibody or fragments thereof so that the antibody or fragments thereof are produced. In some embodiments, the method comprises culturing a host cell comprising nucleic acid encoding an anti-influenza A H7N9 virus antibody of the present invention (or fragments thereof) so that the nucleic acid is expressed. The method may further comprise recovering the anti-influenza A H7N9 virus antibody or fragments thereof from the host cell culture or the host cell culture medium.

The invention also provides a pharmaceutical formulation comprising an anti-influenza A H7N9 virus antibody of the present invention and a pharmaceutically acceptable carrier. The pharmaceutical formulation may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody, or an anti-M2 antibody; etc).

The invention also provides compositions comprising an anti-influenza A H7N9 virus antibody of the present invention. The composition may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody or an anti-M2 antibody; etc).

The invention also provides a composition comprising an anti-influenza A H7N9 virus antibody of the present invention for use in preventing influenza A H7N9 virus infection. In some embodiments, the invention provides a pharmaceutical composition comprising an anti-influenza A H7N9 virus antibody of the present invention for use in preventing influenza A H7N9 virus infection. The invention further provides a composition comprising an anti-influenza A H7N9 virus antibody of the present invention for use in treating influenza A H7N9 virus infection. In some embodiments, the invention provides a pharmaceutical composition comprising an anti-influenza A H7N9 virus antibody of the present invention for use in treating influenza A H7N9 virus infection. The invention further provides a composition comprising an anti-influenza A H7N9 virus antibody of the present invention for use in inhibiting influenza A H7N9 virus infection. In some embodiments, the invention provides a pharmaceutical composition comprising an anti-influenza A H7N9 virus antibody of the present invention for use in inhibiting or neutralizing influenza A H7N9 virus infection.

Compositions comprising an anti-influenza A H7N9 virus antibody of the present invention may also be used in the manufacture of a medicament. The medicament may be for use in the inhibition, treatment, or prevention of influenza A H7N9 virus infection. In certain embodiments, the medicament may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody, or an anti-M2 antibody; etc).

The invention also provides a method for inhibiting influenza A H7N9 virus infection, the method comprising administering to a patient in need thereof an effective amount of a composition comprising an anti-influenza A H7N9 virus antibody of the present invention, thereby inhibiting influenza A virus infection. The invention also provides a method for treating influenza A H7N9 virus infection, the method comprising administering to a patient in need thereof an effective amount of a composition comprising an anti-influenza A H7N9 virus antibody of the present invention, thereby treating influenza A H7N9 virus infection. The invention also provides a method for preventing influenza A H7N9 virus infection, the method comprising administering to a patient in need thereof an effective amount of a composition comprising an anti-influenza A H7N9 virus antibody of the present invention, thereby preventing influenza A H7N9 virus infection. The invention also provides a method for neutralizing influenza A H7N9 virus, the method comprising providing an effective amount of a composition comprising an anti-influenza A H7N9 virus antibody of the present invention, thereby neutralizing influenza A H7N9 virus infection.

The invention also provides a method for inhibiting, treating, or preventing influenza A H7N9 virus infection, the method comprising administering to a patient in need thereof an effective amount of a composition comprising an anti-influenza A H7N9 virus antibody of the present invention, and administering to the patient an effective amount of an additional therapeutic agent, thereby inhibiting, treating, or preventing influenza A H7N9 virus infection. In some embodiments, the additional therapeutic agent is a neuraminidase inhibitor, such as oseltamivir, zanamivir, or peramivir. In other embodiments, the additional therapeutic agent is another anti-influenza A H7N9 virus antibody. In other embodiments, the additional therapeutic agent is another anti-hemagglutinin antibody. In yet other embodiments, the additional therapeutic agent is an anti-M2 antibody. In various aspects of such combination treatments, the therapeutic agents are administered at about the same time, are administered together, or are administered sequentially or consecutively. In particular embodiments, an anti-neuraminidase inhibitor is administered prior to the administration of an anti-influenza A H7N9 virus antibody of the present invention.

In another aspect, the invention provides use of an anti-influenza A H7N9 virus antibody of the present invention in the manufacture of a medicament. The medicament may be for use in the inhibition, treatment, or prevention of influenza A H7N9 virus infection. In certain embodiments, the medicament may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody or an anti-M2 antibody; etc).

In another aspect, the invention provides use of a nucleic acid of the invention in the manufacture of a medicament. The medicament may be for use in the inhibition, treatment, or prevention of influenza A H7N9 virus infection. The medicament may also be for use in neutralizing influenza A H7N9 virus infection. In certain embodiments, the medicament may further comprise an additional therapeutic agent (e.g., a neuraminidase inhibitor, such as oseltamivir, zanamivir, peramivir; another antibody, such as another anti-influenza A H7N9 virus antibody, another anti-hemagglutinin antibody, or an anti-M2 antibody; etc).

In another aspect, the invention provides use of an expression vector of the invention in the manufacture of a medicament. The medicament may be for use in the inhibition, treatment, or prevention of influenza A H7N9 virus infection. The medicament may also be for use in neutralizing influenza A H7N9 virus infection. In certain embodiments, the medicament may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody, or an anti-M2 antibody; etc).

In another aspect, the invention provides use of a host cell of the invention in the manufacture of a medicament. The medicament may be for use in the inhibition, treatment, or prevention of influenza A H7N9 virus infection. The medicament may also be for use in neutralizing influenza A H7N9 virus infection. In certain embodiments, the medicament may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody, or an anti-M2 antibody; etc).

In another aspect, the invention provides use of an article of manufacture of the invention in the manufacture of a medicament. The medicament may be for use in the inhibition, treatment, or prevention of influenza A H7N9 virus infection. The medicament may also be for use in neutralizing influenza A H7N9 virus infection. In certain embodiments, the medicament may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody, or an anti-M2 antibody; etc).

In another aspect, the invention provides use of a kit of the invention in the manufacture of a medicament. The medicament may be for use in the inhibition, treatment, or prevention of influenza A H7N9 virus infection. The medicament may also be for use in neutralizing influenza A H7N9 virus infection. In certain embodiments, the medicament may further comprise an additional therapeutic agent (e.g., a neuraminidase inhibitor, such as oseltamivir, zanamivir, or peramivir; another antibody, such as another anti-influenza A H7N9 virus antibody, another anti-hemagglutinin antibody, or an anti-M2 antibody; etc).

In various aspects, an anti-influenza A H7N9 virus antibody of the present invention binds H7 hemagglutinin. In some aspects, an anti-influenza A H7N9 virus antibody of the present invention binds H7 hemagglutinin of an influenza A H7N9 virus. In other aspects, an anti-influenza A H7N9 virus antibody of the present invention binds H7 hemagglutinin and neutralizes influenza A H7N9 virus. In some embodiments, an anti-influenza A H7N9 virus antibody of the present invention neutralizes influenza A H7N9 virus in vitro, in vivo, or in vitro and in vivo.

BRIEF DESCRIPTION OF THE FIGURES

FIGS. 3A and 3B show the amino acid sequence of the heavy chain, light chain, heavy chain variable region, and light chain variable region for mAb1.

FIGS. 4A and 4B show the amino acid sequence of the heavy chain, light chain, heavy chain variable region, and light chain variable region for mAb2.

FIGS. 5A and 5B show the amino acid sequence of the heavy chain, light chain, heavy chain variable region, and light chain variable region for mAb3.

FIG. 6 shows the amino acid sequence of the heavy chain and light chain hypervariable regions (i.e., CDRs) for mAb1, mAb2, and mAb3.

FIG. 7 shows the nucleic acid sequence of H7 hemagglutinin from influenza A H7N9 virus A/Anhui/1/2013.

FIG. 8 shows the nucleic acid sequence of H7 hemagglutinin from influenza A H7N9 virus A/Shanghai/1/2013.

DETAILED DESCRIPTION OF EMBODIMENTS OF THE INVENTION

I. Definitions

Figure 1A:
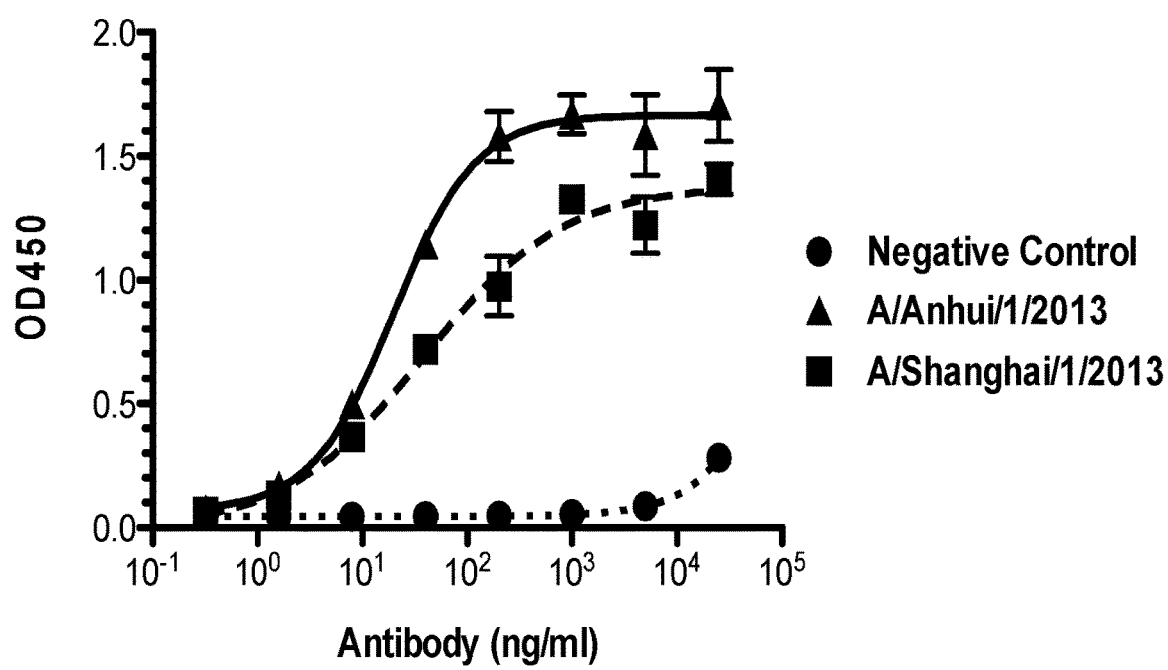
FIGS. 1A, 1B, and 1C set forth data showing mAb1, mAb2, and mAb3 bind to H7 hemagglutinin by ELISA, respectively.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-hemagglutinin antibody" and "an antibody that binds to hemagglutinin" refer to an antibody that binds hemagglutinin with sufficient affinity such that the antibody is useful as a diagnostic and/or therapeutic agent in targeting hemagglutinin, including targeting hemagglutinin of influenza virus. In one embodiment, the extent of binding of an anti-hemagglutinin antibody to an unrelated, non-hemagglutinin protein is less than about 10% of the binding of the antibody to hemagglutinin as measured, e.g., by a radioimmunoassay (RIA). In certain embodiments, an antibody that binds to hemagglutinin has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$M to $10^{-13}$M, e.g., from $10^{-9}$M to $10^{-13}$M). In certain embodiments, an anti-hemagglutinin antibody binds to an epitope of hemagglutinin that is conserved among hemagglutinin from different strains, subtypes, and isolates of influenza A viruses.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. An antibody fragment also refers to a molecule other than an intact antibody that comprises a portion of an intact antibody that binds hemagglutinin and neutralizes influenza A virus. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgA$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-hemagglutinin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "hemagglutinin," as used herein, refers to any native hemagglutinin from any influenza virus source, unless otherwise indicated. The term encompasses "full-length," unprocessed hemagglutinin as well as any form of hemagglutinin that results from processing in an influenza virus or an influenza virus-infected cell. The term also encompasses naturally occurring variants of hemagglutinin, e.g., splice variants or allelic variants. The term "hemagglutinin" as used herein includes H7 hemaglutinin.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease (e.g., preventing occurrence or recurrence of influenza A H7N9 virus infection), reduction (e.g., reducing) or alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-influenza A H7N9 virus antibodies and uses thereof. In certain embodiments, antibodies that bind to H7 hemagglutinin are provided. Antibodies of the invention are useful, e.g., for the diagnosis, treatment, or prevention of influenza A H7N9 virus infection.

A. Exemplary Antibodies to Avian Influenza A H7N9 Virus

In one aspect, the invention provides isolated antibodies that bind to H7 hemagglutinin. In certain embodiments, an anti-influenza A H7N9 virus antibody of the present invention binds H7 hemagglutinin. In other embodiments, an anti-influenza A H7N9 virus antibody of the present invention neutralizes influenza A H7N9 virus in vitro. In other embodiments, an anti-influenza A H7N9 virus antibody of the present invention neutralizes influenza A H7N9 virus in vivo. In yet other embodiments, an anti-influenza A H7N9 virus antibody of the present invention reduces influenza A H7N9 virus infection, prevents influenza A H7N9 virus infection, inhibits influenza A H7N9 virus infection, or treats influenza A H7N9 virus infection. In some embodiments, an anti-influenza A H7N9 virus antibody of the present invention prevents, inhibits, or reduces hemagglutinin-mediated fusion between influenza virus membrane and infected cell endosomal membranes (thus preventing, inhibiting, or reducing viral RNA entry into the infected cell cytoplasm, thus preventing, inhibiting, or reducing further propagation of influenza virus infection.)

In some embodiments, an isolated anti-hemagglutinin antibody (an isolated anti-influenza A H7N9 virus antibody) of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:56;
(b) HVR-H2 comprises the amino acid sequence of SEQ ID NO:57;
(c) HVR-H3 comprises the amino acid sequence of SEQ ID NO:58;
(d) HVR-L1 comprises the amino acid sequence of SEQ ID NO:59;
(e) HVR-L2 comprises the amino acid sequence of SEQ ID NO:60; and
(f) HVR-L3 comprises the amino acid sequence of SEQ ID NO:61.

In some embodiments, the invention provides an isolated anti-hemagglutinin antibody (an isolated anti-influenza A H7N9 virus antibody) comprising: at least one, two, three, four, five and/or six hypervariable region (HVR) sequences, wherein:
(a) HVR-H1 comprises the amino acid sequence of SEQ ID NO:56;
(b) HVR-H2 comprises the amino acid sequence of SEQ ID NO:57;
(c) HVR-H3 comprises the amino acid sequence of SEQ ID NO:58;
(d) HVR-L1 comprises the amino acid sequence of SEQ ID NO:59;
(e) HVR-L2 comprises the amino acid sequence of SEQ ID NO:60; and
(f) HVR-L3 comprises the amino acid sequence of SEQ ID NO:61.

In some embodiments, the invention provides an isolated anti-hemagglutinin antibody (an isolated anti-influenza A H7N9 virus antibody) comprising three light chain hypervariable regions (HVR-L1, HVR-L2, and LVR-L3), wherein:
(a) HVR-L1 comprises the amino acid sequence of SEQ ID NO:59;
(b) HVR-L2 comprises the amino acid sequence of SEQ ID NO:60; and
(c) HVR-L3 comprises the amino acid sequence of SEQ ID NO:61.

In some embodiments, the invention provides an isolated anti-hemagglutinin antibody (an isolated anti-influenza A H7N9 virus antibody) comprising three heavy chain hypervariable regions (HVR-H1, HVR-H2, and HVR-H3), wherein:
(a) HVR-H1 comprises the amino acid sequence of SEQ ID NO:56;
(b) HVR-H2 comprises the amino acid sequence of SEQ ID NO:57; and
(c) HVR-H3 comprises the amino acid sequence of SEQ ID NO:58.

In some embodiments, the invention provides an isolated anti-hemagglutinin antibody (an isolated anti-influenza A H7N9 virus antibody) comprising: at least one, two, and/or three light chain hypervariable region (HVR) sequences, wherein:
(a) HVR-L1 comprises the amino acid sequence of SEQ ID NO:59;
(b) HVR-L2 comprises the amino acid sequence of SEQ ID NO:60; and
(c) HVR-L3 comprises the amino acid sequence of SEQ ID NO:61.

In some embodiments, the invention provides an isolated anti-hemagglutinin antibody (an isolated anti-influenza A H7N9 virus antibody) comprising: at least one, two, and/or three heavy chain hypervariable region (HVR) sequences, wherein:
(a) HVR-H1 comprises the amino acid sequence of SEQ ID NO:56;
(b) HVR-H2 comprises the amino acid sequence of SEQ ID NO:57; and
(c) HVR-H3 comprises the amino acid sequence of SEQ ID NO:58.

In some embodiments, an isolated anti-hemagglutinin antibody (an isolated anti-influenza A H7N9 virus antibody) of the present invention comprises a heavy chain variable region and a light chain variable region, wherein the heavy chain variable region comprises the amino acid sequence of SEQ ID NO:74, and the light chain variable region comprises the amino acid sequence of SEQ ID NO:75.

In some embodiments, an isolated anti-hemagglutinin antibody (an isolated anti-influenza A H7N9 virus antibody) of the present invention comprises a light chain variable region comprising the amino acid sequence of SEQ ID NO:75.

In some embodiments, an isolated anti-hemagglutinin antibody (an isolated anti-influenza A H7N9 virus antibody) of the present invention comprises a heavy chain variable region comprises the amino acid sequence of SEQ ID NOs:74.

In some embodiments, an isolated anti-hemagglutinin antibody (an isolated anti-influenza A H7N9 virus antibody) of the present invention comprises a heavy chain and a light chain, wherein the heavy chain comprises the amino acid sequence of SEQ ID NO:76, and the light chain comprises the amino acid sequence of SEQ ID NO:77.

In some embodiments, an isolated anti-hemagglutinin antibody (an isolated anti-influenza A H7N9 virus antibody) of the present invention comprises a light chain comprising the amino acid sequence of SEQ ID NO:77.

In some embodiments, an isolated anti-hemagglutinin antibody (an isolated anti-influenza A H7N9 virus antibody) of the present invention comprises a heavy chain comprising the amino acid sequence of SEQ ID NO:76.

In some embodiments, the present invention provides a method for preventing or treating influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
  (a) HVR-H1 comprises the amino acid sequence of SEQ ID NO:56;
  (b) HVR-H2 comprises the amino acid sequence of SEQ ID NO:57;
  (c) HVR-H3 comprises the amino acid sequence of SEQ ID NO:58;
  (d) HVR-L1 comprises the amino acid sequence of SEQ ID NO:59;
  (e) HVR-L2 comprises the amino acid sequence of SEQ ID NO:60; and
  (f) HVR-L3 comprises the amino acid sequence of SEQ ID NO:61.

In some embodiments, the present invention provides a method for preventing or treating influenza A H7N9 virus infection, the method comprising administering to a subject having or at risk for having influenza A H7N9 virus infection a therapeutically effective amount of an antibody, wherein the antibody comprises a heavy chain variable region and a light chain variable region, wherein the heavy chain variable region comprises the amino acid sequence of SEQ ID NO:74, and wherein the light chain variable region comprises the amino acid sequence of SEQ ID NO:75.

In some embodiments, the present invention provides a method for preventing or treating influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain comprises the amino acid sequence of SEQ ID NO:76, and the light chain comprises the amino acid sequence of SEQ ID NO:77.

In some embodiments, an isolated anti-hemagglutinin antibody (an isolated anti-influenza A H7N9 virus antibody) of the present invention comprises three heavy chain hypervariable regions (HVR-H1, HVR-H2, and HVR-H3) and three light chain hypervariable regions (HVR-L1, HVR-L2, and HVR-L3), wherein:
  (a) HVR-H1 comprises the amino acid sequence of SEQ ID NO:62;
  (b) HVR-H2 comprises the amino acid sequence of SEQ ID NO:63;
  (c) HVR-H3 comprises the amino acid sequence of SEQ ID NO:64;
  (d) HVR-L1 comprises the amino acid sequence of SEQ ID NO:65;
  (e) HVR-L2 comprises the amino acid sequence of SEQ ID NO:66; and
  (f) HVR-L3 comprises the amino acid sequence of SEQ ID NO:67.

In some embodiments, the invention provides an isolated anti-hemagglutinin antibody (an isolated anti-influenza A H7N9 virus antibody) comprising: at least one, two, three, four, five and/or six hypervariable region (HVR) sequences, wherein:
  (a) HVR-H1 comprises the amino acid sequence of SEQ ID NO:62;
  (b) HVR-H2 comprises the amino acid sequence of SEQ ID NO:63;
  (c) HVR-H3 comprises the amino acid sequence of SEQ ID NO:64;
  (d) HVR-L1 comprises the amino acid sequence of SEQ ID NO:65;
  (e) HVR-L2 comprises the amino acid sequence of SEQ ID NO:66; and
  (f) HVR-L3 comprises the amino acid sequence of SEQ ID NO:67.

In some embodiments, the invention provides an isolated anti-hemagglutinin antibody (an isolated anti-influenza A H7N9 virus antibody) comprising three light chain hypervariable regions (HVR-L1, HVR-L2, and LVR-L3), wherein:
  (a) HVR-L1 comprises the amino acid sequence of SEQ ID NO:65;
  (b) HVR-L2 comprises the amino acid sequence of SEQ ID NO:66; and
  (c) HVR-L3 comprises the amino acid sequence of SEQ ID NO:67.

In some embodiments, the invention provides an isolated anti-hemagglutinin antibody (an isolated anti-influenza A H7N9 virus antibody) comprising three heavy chain hypervariable regions (HVR-H1, HVR-H2, and HVR-H3), wherein:
  (a) HVR-H1 comprises the amino acid sequence of SEQ ID NO:62;
  (b) HVR-H2 comprises the amino acid sequence of SEQ ID NO:63; and
  (c) HVR-H3 comprises the amino acid sequence of SEQ ID NO:64.

In some embodiments, the invention provides an isolated anti-hemagglutinin antibody (an isolated anti-influenza A H7N9 virus antibody) comprising: at least one, two, and/or three light chain hypervariable region (HVR) sequences, wherein:
  (a) HVR-L1 comprises the amino acid sequence of SEQ ID NO:65;
  (b) HVR-L2 comprises the amino acid sequence of SEQ ID NO:66; and
  (c) HVR-L3 comprises the amino acid sequence of SEQ ID NO:67.

In some embodiments, the invention provides an isolated anti-hemagglutinin antibody (an isolated anti-influenza A H7N9 virus antibody) comprising: at least one, two, and/or three heavy chain hypervariable region (HVR) sequences, wherein:
  (a) HVR-H1 comprises the amino acid sequence of SEQ ID NO:62;
  (b) HVR-H2 comprises the amino acid sequence of SEQ ID NO:63; and
  (c) HVR-H3 comprises the amino acid sequence of SEQ ID NO:64.

In some embodiments, an isolated anti-hemagglutinin antibody (an isolated anti-influenza A H7N9 virus antibody) of the present invention comprises a heavy chain variable region and a light chain variable region, wherein the heavy chain variable region comprises the amino acid sequence of SEQ ID NO:78, and the light chain variable region comprises the amino acid sequence of SEQ ID NO:79.

In some embodiments, an isolated anti-hemagglutinin antibody (an isolated anti-influenza A H7N9 virus antibody) of the present invention comprises a light chain variable region comprising the amino acid sequence of SEQ ID NO:79.

In some embodiments, an isolated anti-hemagglutinin antibody (an isolated anti-influenza A H7N9 virus antibody)

of the present invention comprises a heavy chain variable region comprises the amino acid sequence of SEQ ID NOs:78.

In some embodiments, an isolated anti-hemagglutinin antibody (an isolated anti-influenza A H7N9 virus antibody) of the present invention comprises a heavy chain and a light chain, wherein the heavy chain comprises the amino acid sequence of SEQ ID NO:80, and the light chain comprises the amino acid sequence of SEQ ID NO:81.

In some embodiments, an isolated anti-hemagglutinin antibody (an isolated anti-influenza A H7N9 virus antibody) of the present invention comprises a light chain comprising the amino acid sequence of SEQ ID NO:81.

In some embodiments, an isolated anti-hemagglutinin antibody (an isolated anti-influenza A H7N9 virus antibody) of the present invention comprises a heavy chain comprising the amino acid sequence of SEQ ID NO:80.

In some embodiments, the present invention provides a method for preventing or treating influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
  (a) HVR-H1 comprises the amino acid sequence of SEQ ID NO:62;
  (b) HVR-H2 comprises the amino acid sequence of SEQ ID NO:63;
  (c) HVR-H3 comprises the amino acid sequence of SEQ ID NO:64;
  (d) HVR-L1 comprises the amino acid sequence of SEQ ID NO:65;
  (e) HVR-L2 comprises the amino acid sequence of SEQ ID NO:66; and
  (f) HVR-L3 comprises the amino acid sequence of SEQ ID NO:67.

In some embodiments, the present invention provides a method for preventing or treating influenza A H7N9 virus infection, the method comprising administering to a subject having or at risk for having influenza A H7N9 virus infection a therapeutically effective amount of an antibody, wherein the antibody comprises a heavy chain variable region and a light chain variable region, wherein the heavy chain variable region comprises the amino acid sequence of SEQ ID NO:78, and the light chain variable region comprises the amino acid sequence of SEQ ID NO:79.

In some embodiments, the present invention provides a method for preventing or treating influenza A H7N9 virus infection, the method comprising administering to a subject having or at risk for having influenza A H7N9 virus infection a therapeutically effective amount of an antibody, wherein the antibody comprises a heavy chain and a light chain, wherein the heavy chain comprises the amino acid sequence of SEQ ID NO:80, and the light chain comprises the amino acid sequence of SEQ ID NO:81.

In any of the above embodiments, an anti-influenza A H7N9 virus antibody of the present invention is humanized. In one embodiment, an anti-influenza A H7N9 virus antibody comprises HVRs as in any of the above embodiments, and further comprises an acceptor human framework, e.g., a human immunoglobulin framework or a human consensus framework.

In another aspect, an anti-influenza A H7N9 virus antibody of the present comprises a heavy chain variable domain (VH) sequence having at least 90%, 91%, 92%, 93%, 94%, 95%, 96%, 97%, 98%, 99%, or 100% sequence identity to an amino acid sequence selected from the group consisting of SEQ ID NOs:74 and 78. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-influenza A H7N9 virus antibody comprising that sequence retains the ability to bind to H7 hemagglutinin. In certain embodiments, a total of 1 to 10 amino acids have been substituted, inserted and/or deleted in SEQ ID NOs:74 or 78. In certain embodiments, substitutions, insertions, or deletions occur in regions outside the HVRs (i.e., in the FRs). Optionally, the anti hemagglutinin antibody (the anti-influenza A H7N9 virus antibody) comprises the VH sequence in SEQ ID NO:74 or 78, including post-translational modifications of that sequence.

In another aspect, an anti-influenza A H7N9 virus antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from the group consisting of SEQ ID NOs:75 and 79. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-influenza A H7N9 virus antibody comprising that sequence retains the ability to bind to H7 hemagglutinin. In certain embodiments, a total of 1 to 10 amino acids have been substituted, inserted and/or deleted in SEQ ID NOs: 75 or 79. In certain embodiments, the substitutions, insertions, or deletions occur in regions outside the HVRs (i.e., in the FRs). Optionally, the anti-hemagglutinin antibody (the anti-influenza A H7N9 virus antibody) comprises the VL sequence in SEQ ID NOs: 75 or 79, including post-translational modifications of that sequence.

In another aspect, an anti-influenza A H7N9 virus antibody is provided, wherein the antibody comprises a VH as in any of the embodiments provided above, and a VL as in any of the embodiments provided above. In one embodiment, the antibody comprises the VH and VL sequences in SEQ ID NOs:74 or 78, and SEQ ID NOs:75 or 79, respectively, including post-translational modifications of those sequences.

In a further aspect, the invention provides an antibody that binds to the same epitope as an anti-influenza A H7N9 virus antibody provided herein. For example, in certain embodiments, an antibody is provided that binds to the same epitope as an anti-influenza A H7N9 virus antibody comprising a VH sequence of SEQ ID NO:75 and a VL sequence of SEQ ID NO:75; or a VH sequence of SEQ ID NO:78 and a VL sequence of SEQ ID NO:79.

In a further aspect of the invention, an anti-influenza A H7N9 virus antibody according to any of the above embodiments is a monoclonal antibody, including a chimeric, humanized, or human antibody. In one embodiment, an anti-influenza A H7N9 virus antibody is an antibody fragment, e.g., a Fv, Fab, Fab', scFv, diabody, or F(ab')$_2$ fragment. In another embodiment, the antibody is a full length antibody, e.g., an intact, e.g., IgG1 antibody or other antibody class or isotype as defined herein.

In a further aspect, an anti-influenza A H7N9 virus antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthiin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.*

13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art or using techniques described herein. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for hemagglutinin and the other is for any other antigen. In certain embodiments, bispecific antibodies may bind to two different epitopes of hemagglutinin. Bispecific antibodies may also be used to localize cytotoxic agents to cells which express hemagglutinin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to hemagglutinin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-hemagglutinin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-hemagglutinin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-hemagglutinin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, N.J., 2003), pp. 245-254, describing expression of antibody fragments in *E. coli*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, N.J.), pp. 255-268 (2003).

C. Assays

Anti-hemagglutinin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding of H7 hemagglutinin with any anti-influenza A H7N9 virus (anti-H7 hemagglutinin) antibody described herein. In certain embodiments, such a competing antibody binds to the same epitope (e.g., a linear or a conformational epitope) that is bound by an anti-influenza A H7N9 virus antibody described here (e.g., an anti-influenza A H7N9 virus antibody comprising a VH sequence of SEQ ID NO:74 and a VL sequence of SEQ ID NO:74; or a VH sequence of SEQ ID NO:78 and a VL sequence of SEQ ID NO:79. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized hemagglutinin is incubated in a solution comprising a first labeled antibody that binds to hemagglutinin and a second unlabeled antibody that is being tested for its ability to compete with the first antibody for binding to hemagglutinin. The second antibody may be present in a hybridoma supernatant. As a control, immobilized hemagglutinin is incubated in a solution comprising the first labeled antibody but not the second unlabeled antibody. After incubation under conditions permissive for binding of the first antibody to hemagglutinin, excess unbound antibody is removed, and the amount of label associated with immobilized hemagglutinin is measured. If the amount of label associated with immobilized hemagglutinin is substantially reduced in the test sample relative to the control sample, then that indicates that the second antibody is competing with the first antibody for binding to hemagglutinin. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-influenza A H7N9 virus antibodies and fragments thereof having biological activity. Biological activity may include, e.g., specifically binding to influenza A HyN9 virus hemagglutinin, neutralizing influenza A H7N9 virus, etc. Antibodies and compositions comprising antibodies or fragments thereof having such biological activity in vivo and/or in vitro are also provided.

In certain embodiments, an antibody of the invention is tested for such biological activity. See Examples 4, 5, 6, 7, 8, and 9 for exemplary descriptions of such assays.

D. Immunoconjugates

The invention also provides immunoconjugates comprising an anti-influenza A H7N9 virus antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-STAB, sulfo-SMCC, and sulfo-SMPB, and SVSB (succinimidyl-(4-vinyl sulfone)benzoate) which are commercially available (e.g., from Pierce Biotechnology, Inc., Rockford, Ill., U.S.A).

E. Methods and Compositions for Diagnostics and Detection

In certain embodiments, any of the anti-influenza A H7N9 virus antibodies provided herein is useful for detecting the presence of H7 hemagglutinin or influenza A H7N9 virus in a biological sample. The term "detecting" as used herein encompasses quantitative or qualitative detection. In certain embodiments, a biological sample comprises a cell or tissue, such as, for example, lung, upper respiratory tract, nasal canal, blood, sputum, or comprises a biological sample obtained by nasal or throat swab.

In one embodiment, an anti-influenza A H7N9 virus antibody for use in a method of diagnosis or detection is provided. In a further aspect, a method of detecting the presence of H7 hemagglutinin or influenza A H7N9 virus in a biological sample is provided. In certain embodiments, the method comprises contacting the biological sample with an anti-influenza A H7N9 virus antibody as described herein under conditions permissive for binding of the anti-influenza A H7N9 virus antibody to H7 hemagglutinin, and detecting whether a complex is formed between the anti-influenza A H7N9 virus antibody and H7 hemagglutinin. Such method may be an in vitro or in vivo method. In one embodiment, an anti-influenza A H7N9 virus antibody is used to select subjects eligible for therapy with an anti-influenza A H7N9 virus antibody, e.g., where H7 hemagglutinin is a biomarker for selection of patients.

Exemplary disorders that may be diagnosed using an antibody of the invention include influenza A H7N9 virus infection, including influenza A H7N9 virus infection in children, infants, adults, and the elderly, as well as in birds.

In certain embodiments, labeled anti-influenza A H7N9 virus antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-hemagglutinin antibody (e.g., anti-H7 hemagglutinin antibody, anti-influenza A H7N9 virus antibody) as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Application Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a neuraminidase inhibitor, an anti-hemagglutinin antibody, an anti-M2 antibody, etc. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-hemagglutinin antibodies (e.g., an anti-H7 hemagglutinin antibody, an anti-influenza A H7N9 virus antibody) provided herein may be used in therapeutic methods.

In one aspect, an anti-hemagglutinin antibody (e.g., an anti-H7 hemagglutinin antibody, an anti-influenza A H7N9 virus antibody) for use as a medicament is provided. In further aspects, an anti-hemagglutinin antibody (e.g., an anti-H7 hemagglutinin antibody, an anti-influenza A H7N9 virus antibody) for use in treating, preventing, or inhibiting influenza A H7N9 virus infection is provided. In certain embodiments, an anti-hemagglutinin antibody (e.g., an anti-H7 hemagglutinin antibody, an anti-influenza A H7N9 virus antibody) for use in a method of treatment is provided. In certain embodiments, the invention provides an anti-hemagglutinin antibody (e.g., an anti-H7 hemagglutinin antibody, an anti-influenza A H7N9 virus antibody) for use in a method of treating an individual having influenza A H7N9 virus infection comprising administering to the individual an effective amount of the anti-hemagglutinin antibody (e.g., an anti-H7 hemagglutinin antibody, an anti-influenza A H7N9 virus antibody). In one such embodiment, the method further comprises administering to the individual an effective amount of at least one additional therapeutic agent, e.g., as described below. In further embodiments, the invention provides an anti-hemagglutinin antibody (e.g., an anti-H7 hemagglutinin antibody, an anti-influenza A H7N9 virus antibody) for use in preventing, inhibiting, or reducing hemagglutinin-mediated fusion between influenza A H7N9 virus viral membrane and infected cell endosomal membranes, thus preventing viral RNA entry into the infected cell cytoplasm and preventing further propagation of infection. In certain embodiments, the invention provides an anti-hemagglutinin antibody (e.g., an anti-H7 hemagglutinin antibody, an anti-influenza A H7N9 virus antibody) for use in a method of preventing, inhibiting, or treating influenza A H7N9 virus infection in an individual comprising administering to the individual an effective amount of the anti-hemagglutinin antibody (e.g., an anti-H7 hemagglutinin antibody, an anti-influenza A H7N9 virus antibody) to prevent, inhibit, or treat influenza A H7N9 virus infection. An "individual" according to any of the above embodiments is preferably a human.

In a further aspect, the invention provides for the use of an anti-hemagglutinin antibody (e.g., an anti-H7 hemagglutinin antibody, an anti-influenza A H7N9 virus antibody) in the manufacture or preparation of a medicament. In one embodiment, the medicament is for treatment of influenza A H7N9 virus infection. In a further embodiment, the medicament is for use in a method of treating influenza A H7N9 virus infection comprising administering to an individual having influenza A H7N9 virus infection an effective amount of the medicament. In one such embodiment, the method further comprises administering to the individual an effective amount of at least one additional therapeutic agent, e.g., as described below. In a further embodiment, the medicament is for preventing, inhibiting, or reducing hemagglutinin-mediated fusion between influenza A H7N9 virus viral membrane and infected cell endosomal membranes, thus preventing viral RNA entry into the infected cell cytoplasm and preventing further propagation of infection. In a further embodiment, the medicament is for use in a method of preventing, inhibiting, or treating influenza A H7N9 virus infection in an individual comprising administering to the individual an amount effective of the medicament to prevent, inhibit, or reduce, influenza A H7N9 virus infection. An "individual" according to any of the above embodiments may be a human.

In a further aspect, the invention provides a method for treating influenza A H7N9 virus infection. In one embodiment, the method comprises administering to an individual having such influenza A H7N9 virus infection an effective amount of an anti-hemagglutinin antibody (e.g., an anti-H7 hemagglutinin antibody, an anti-influenza A H7N9 virus antibody). In one such embodiment, the method further comprises administering to the individual an effective amount of at least one additional therapeutic agent, as described herein. An "individual" according to any of the above embodiments may be a human.

The present invention provides anti-hemagglutinin antibodies (e.g., anti-H7 hemagglutinin antibodies, anti-influenza A H7N9 virus antibodies) effective at inhibiting, preventing, or treating influenza A H7N9 virus infection in an individual (e.g., a subject or a patient). In some aspects, an anti-hemagglutinin antibody (e.g., an anti-H7 hemagglutinin antibody, an anti-influenza A H7N9 virus antibody) of the present invention is effective at prophylactically treating an individual in order to prevent influenza A H7N9 virus infection of the individual.

In some aspects, an individual suitable for treatment with an anti-hemagglutinin antibody (e.g., an anti-H7 hemagglutinin antibody, an anti-influenza A H7N9 virus antibody) of the present invention is an individual having or suspected having influenza A H7N9 virus infection. In some embodiments, such individuals include infants, children, adults, and the elderly. In some embodiments, the individual is hospitalized with influenza A H7N9 virus infection. In other embodiments, the individual having influenza A H7N9 virus infection has one or more co-morbidities, such as, for example, immunodeficiency, pregnancy, lung disease, heart disease, renal disease, or co-infection (e.g., a bacterial infection or a viral infection, such as bacterial or viral pneumonia).

In some aspects, treatment of an individual with an anti-hemagglutinin antibody (e.g., an anti-H7 hemagglutinin antibody, an anti-influenza A H7N9 virus antibody) of the present invention reduces influenza A H7N9 virus infection severity, reduces the length of influenza A H7N9 virus infection, or reduces influenza A H7N9 virus infectivity. In other aspects, treatment of influenza A H7N9 virus infection with an anti-hemagglutinin antibody (e.g., an anti-H7 hemagglutinin antibody, an anti-influenza A H7N9 virus antibody) of the present invention provides additional benefit, including a reduction in the length of hospital stay, reduction or prevention of the need for intensive care unit (ICU) use, reduction or prevention of the need for assisted or mechanical ventilation, reduction or prevention of the need for supplemental oxygen use, and reduction of mortality. In some aspects, the reduction in the length of hospital stay is 1 day, 2 days, 3 days, 4 days, 5 days, or longer than 5 days. In some aspects, the reduction in the need for intensive care unit use is 1 day, 2 days, 3 days, 4 days, 5 days, or longer than 5 days. In some aspects, the reduction in need for assisted or mechanical ventilation is 1 day, 2 days, 3 days, 4 days, 5 days, or longer than 5 days. In some aspects, the reduction in the need for supplemental oxygen is 1 day, 2 days, 3 days, 4 days, 5 days, or longer than 5 days. In some aspects, treatment of an individual with an anti-hemagglutinin antibody of the present invention reduces influenza A H7N9 virus infection disease symptoms, such as, for example, fever, coryza, chills, sore throat, muscle pain, body aches, headache, cough, nasal congestion, weakness or fatigue, irritated or watering eyes, and general discomfort.

In some aspects, treatment of an individual with an anti-hemagglutinin antibody (e.g., an anti-H7 hemagglutinin antibody, an anti-influenza A H7N9 virus antibody) of the present invention reduces the time to normalization of respiratory function, such as a reduction of time to normalization of respiratory rate, or a reduction of time to normalization of oxygen saturation. In some aspects, treatment of an individual with an anti-hemagglutinin antibody of the present invention reduces the time to return to normal oxygen saturation, e.g., to an oxygen saturation of about 92% or greater, as measured over a 24 hour period without supplemental oxygen administration. In other aspects, treatment of an individual with an anti-hemagglutinin antibody (e.g., an anti-H7 hemagglutinin antibody, an anti-influenza A H7N9 virus antibody) of the present invention reduces the time to normalization of vital signs, such as heart rate, blood pressure, respiratory rate, and temperature.

In some aspects, treatment of an individual with an anti-hemagglutinin antibody (e.g., an anti-H7 hemagglutinin antibody, an anti-influenza A H7N9 virus antibody) of the present invention improves virologic endpoints, such as, for example, influenza A H7N9 virus titer. Virus titer can be measured by various ways known to one of skill in the art, such as, for example, viral area under the curve (AUC), as measured by, for example, qPCR or tissue culture infective does (TCID50). In some aspects, the treatment results in greater than or equal to 50% reduction in viral AUC as measured by qPCR or TCID50.

In various aspects of the present invention, an anti-hemagglutinin antibody (e.g., an anti-H7 hemagglutinin antibody, an anti-influenza A H7N9 virus antibody) provided herein is effective at treating influenza A H7N9 virus infection when administered at about 12 hours, at about 24 hours, at about 36 hours, at about 48 hours, at about 60 hours, at about 72 hours, at about 84 hours, and at about 96 hours after onset of symptoms (e.g., after onset of illness). In other aspects, an anti-hemagglutinin antibody (e.g., an anti-H7 hemagglutinin antibody, an anti-influenza A H7N9 virus antibody) provided herein is effective at treating influenza A H7N9 virus infection when administered between about 24 hours and 48 hours after onset of symptoms (e.g., the individual has been symptomatic for between 24 and 48 hours), when administered between about 48 hours and 72 hours after onset of symptoms, or when administered between about 72 hours and 96 hours after onset of symptoms. In certain embodiments of the present invention, an anti-hemagglutinin antibody (e.g., an anti-H7 hemagglutinin antibody, an anti-influenza A H7N9 virus antibody) of the present invention is effective at treating or reducing influenza A H7N9 virus infection and extends the treatment window of current standard of care (e.g., oseltamivir) beyond 48 hours after onset of symptoms.

In a further aspect, the invention provides pharmaceutical formulations comprising any of the anti-hemagglutinin antibodies provided herein, e.g., for use in any of the above therapeutic methods. In one embodiment, a pharmaceutical formulation comprises any of the anti-hemagglutinin antibodies provided herein and a pharmaceutically acceptable carrier. In another embodiment, a pharmaceutical formulation comprises any of the anti-hemagglutinin antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a neuraminidase inhibitor (e.g., zanamivir, oseltamivir phosphate, peramivir, amantadine, rimantadine), an anti-M2 antibody, an anti-hemagglutinin antibody, etc. In some aspects, treatment of an individual having influenza A H7N9 virus infection with an anti-hemagglutinin antibody of the present invention co-administered with a neuraminidase inhibitor provides a synergistic therapeutic effect compared to treatment with either agent alone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-hemagglutinin antibody and administration of an additional therapeutic agent occur within about one month, or within about one, two, or three weeks, within about one, two, three, four, five, or six days, or within about one, two, three, four, five, six, eight, ten, twelve, sixteen, twenty, or twenty-four hours of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to about 45 mg/kg (e.g., about 1.0 mg/kg to about 15 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. Exemplary dosages of the antibody would be in the range from about 1.0 mg/kg to about 45 mg/kg, from about 1.0 mg/kg to about 30 mg/kg, from about 1.0 mg/kg to about 15 mg/kg, from about 1.0 mg/kg to about 10 mg/kg, or from about 1.0 mg/kg to about 5 mg/kg. Thus, one or more doses of about 1.0 mg/kg, 2.5 mg/kg, 5.0 mg/kg, 10 mg/kg, 15 mg/kg, 30 mg/kg, or 45 mg/kg (or any combination thereof) may be administered to the patient. Such doses may be administered intermittently, e.g., every day, every two days, every three days, etc. An initial higher loading dose, followed by one or more lower doses may be administered. Dosing can also be at a fixed dose, such as, for example, 200 mg, 400 mg, 600 mg, 800 mg, 1000 mg, 1200 mg, 1400 mg, 1500 mg, 1600 mg, 1800 mg, 2000 mg, 2200 mg, 2400 mg, 2500 mg, 2600 mg, 2800 mg, 3000 mg, 3200 mg, 3400 mg, 3600 mg, etc. The progress of this therapy is easily monitored by conventional techniques and assays.

It is understood that any of the above formulations or therapeutic methods may be carried out using an immunoconjugate of the invention in place of or in addition to an anti-hemagglutinin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-hemagglutinin antibody.

III. Examples

The following are examples of methods and compositions of the invention. It is understood that various other embodiments may be practiced, given the general description provided above.

Example 1

Identification of Anti-Hemagglutinin Antibodies by Phage Display

Anti-influenza virus mAb3 described herein was identified by phage display using a phage display library constructed from peripheral blood mononuclear cells (PBMCs) isolated from human donors vaccinated with the seasonal influenza virus vaccine as follows, as previously described. (See U.S. patent application Ser. No. 14/077,414, which is incorporated by reference herein in its entirety.)

Example 2

Plasmablast Enrichment and Expansion

Anti-influenza A H7N9 virus mAb1 and anti-influenza A H7N9 virus mAb2 described herein were identified using a plasmablast enrichment and expansion technique as previously described. (See Nakamura et al. (2013) Cell Host & Microbe 14:93-103 and U.S. patent application Ser. No. 14/077,414, each of which is incorporated by reference herein in its entirety.)

Leukopacs from normal human donors that received the seasonal influenza Fluvirin® vaccine (Novartis Lot #111796P1) 7 days prior to their blood donation were obtained from Blood Centers of the Pacific (San Francisco, Calif.). Peripheral blood mononuclear cells (PBMCs) were isolated from the leukopacs using standard methodologies. Six- to eight-week old female SCID/beige mice were purchased from Charles River Laboratories (Hollister, Calif.) and housed and maintained at Genentech in accordance with American Association of Laboratory Animal Care guidelines. All experimental studies were conducted under the approval of the Institutional Animal Care and Use Committees of Genentech Lab Animal Research in an AAALACi-accredited facility in accordance with the Guide for the Care and Use of Laboratory Animals and applicable laws and regulations. Leukopac or blood from healthy human donors was obtained after written informed consent was provided and ethical approval granted from the Western Institutional Review Board.

In vivo antigen-driven plasmablast enrichment and expansion was performed using intraspenic transplantation of PBMCs as follows. Isolated PBMCs were resuspended with hemagglutinin antigens (0.1-2 µg for each one million B cells) and incubated for 30 minutes at 37° C. (PBMC/antigen pre-mix). Following this incubation, the PBMCs were washed to remove unbound antigens. To enrich for plasmablasts that produced cross-reactive hemagglutinin antibodies, the hemagglutinin antigen variants used for PBMC/antigen pre-mix and single cell sorting were specifically chosen to differ from the hemagglutinin antigen variants contained within the influenza Fluvirin® vaccine. Hemagglutinin antigens used in this study, therefore, included H1 hemagglutinin from influenza A virus isolate A/NWS/1933, H3 hemagglutinin from influenza A virus isolate A/Hong Kong/8/1968, and H7 hemagglutinin from influenza A virus isolate A/Netherlands/219/2003. The hemagglutinin antigens were produced at Genentech using standard molecular biology techniques.

6-8 week old female SCID/beige mice (Charles River Laboratories, Hollister, Calif.) were sub-lethally irradiated with 350 rads using a Cesium-137 source. Polymyxin B (110 mg/L) and neomycin (1.1 g/L) were added to the drinking water for 7 days following irradiation. Four hours after irradiation, the left flank of each mouse was shaved and prepped with Betadine® (Purdue Pharma, Stamford, Conn.) and 70% alcohol. Surgical procedures were performed under anesthesia using aseptic surgical procedures. A 1-cm skin incision was made just below the costal border of each mouse, followed by an incision of the abdominal wall and the peritoneum. The spleen of each mouse was carefully exposed and injected with $50\times10^6$ human PBMCs resuspened in 30 μL PBS. The incisions were closed in the muscular layer and in the skin using 5-0 Vicryl® sutures (Ethicon, Somerville, N.J.) and surgical staples, respectively. For antigen-specific cell sorting experiments, mice were sacrificed at 8 days post-transplantation, and their spleens harvested.

Single cell suspensions of spleen cells obtained from the mice were stained with a cocktail of anti-human monoclonal antibodies CD38 PECy7 (BD Biosciences, San Jose, Calif.) and IgG Dylight (Jackson ImmunoResearch Laboratories, Inc., West Grove, Pa.) which define human IgG+ plasmablasts as $CD38^{high}$/IgG+ expression. To identify hemagglutinin cross-reactive plasmablasts within the suspension of isolated spleen cells, the cells were stained with hemagglutinin H1 from influenza virus A isolate A/NWS/1933 and hemagglutinin H3 from influenza virus A isolate A/Hong Kong/8/1968, which were previously conjugated with FITC or PE, respectively, using Lightning-Link® labeling kits (Innova Biosciences, Cambridge, UK).

Samples were then analyzed in the presence of propidium iodide dead cell exclusion on Aria high-speed cell sorter (BD Biosciences, San Jose, Calif.) and anti-hemagglutinin-specific plasmablasts were sorted in a single cell manner into 96-well tissue culture plates containing 50 μl RPMI cell cutlute media supplemented with 5% Low IgG fetal bovine serum. (Gibco, Grand Island, N.Y.).

Example 3

IgG Cloning from Single Plasmablasts

Hemagglutinin H1 and H3 cross-reactive human plasmablasts (described above) were single-cell sorted. Single plasmablasts were sorted directly into U-bottom 96-well micro-well plates containing 50 μl RPMI containing 5% Low IgG fetal bovine serum. The plates were centrifuged for 5 minutes at 600×g (Beckman Coulter, Brea, Calif.) and the media was carefully removed by aspiration. The cells were re-suspended and washed twice in 90 μl of PBS following the same procedure.

To generate cDNA encoding the variable heavy chains and light chains, each cell was re-suspended in 6 μl of Reverse Transcriptase (RT) reaction mixture containing 2 units RNaseout (Invitrogen, Grand Island, N.Y.), 0.5 mM 4dNTP (Perkin Elmer, Waltham, Mass.), 1.5 mM $MgCl_2$, 37.5 mM KCl, 10 mM DTT (dithiothreitol), 0.25% Nonidet P40 (US Biological, Marblehead, Mass.), 0.1 mg/ml bovine serum albumin (Sigma-Aldrich), 25 mM Tris pH 8.3, 0.25 pmol of $IgG_{1-4}$ constant, kappa chain constant, and lambda chain constant region specific oligonucleotides (shown below) and 40 U Superscript III (Invitrogen, Grand Island, N.Y.).

```
IgG1-4 constant:
                                    (SEQ ID NO: 1)
GAAGTAGTCCTTGACCAGGCAG Kappa constant:
                                    (SEQ ID NO: 2)
CTCAGCGTCAGGGTGYTGCTGAG Lambda constant:
                                    (SEQ ID NO: 3)
GGGTKTGGTSGTCTCCAC
```

The reaction was incubated for 3×30-minute intervals at 45° C., 50° C., and 55° C. each. Following the incubation, the reaction mixture was diluted to 15 µl with TE buffer (10 mm Tris HCl, 1 mM EDTA). Initial polymerase chain reactions (PCR) were performed to amplify IgG heavy chains, kappa chains, and lambda chains using 2 µl of the diluted RT cocktail from above and Advantage-GC 2 Polymerase Mix (Clontech, Mountain View, Calif.), following protocols provided by the manufacturers. The PCR amplifications were performed using degenerate oligonucleotides based on variable heavy chain and light chain germline and constant region sequences shown below.

```
IGVH1a
                                    (SEQ ID NO: 4)
CAGGTGCAGCTGGTGCAGTCTGGGGC

IGVH1b
                                    (SEQ ID NO: 5)
CAGGTCCAGCTGGTGCAGTCTGGGGC

IGVH2
                                    (SEQ ID NO: 6)
CAGGTCACCTTGAAGGAGTCTGGTCC

IGVH3
                                    (SEQ ID NO: 7)
GAGGTGCAGCTGGTGGAGTCTGGGGG

IGVH4
                                    (SEQ ID NO: 8)
CAGGTGCAGCTGCAGGAGTCGGGCCC

IGVH5
                                    (SEQ ID NO: 9)
GAGGTGCAGCTGGTGCAGTCTGG

IGVH6
                                    (SEQ ID NO: 10)
CAGGTACAGCTGCAGCAGTCAGGTCC

IGVH7
                                    (SEQ ID NO: 11)
CAGGTGCAGCTGGTGCAATCTGG

IGKV1
                                    (SEQ ID NO: 12)
GHCATCCRGWTGACCCAGTCTC

IGKV2
                                    (SEQ ID NO: 13)
GATRTTGTGATGACYCAGWCTC

IGKV3
                                    (SEQ ID NO: 14)
GAAATWGTRWTGACRCAGTCTC

IGKV4
                                    (SEQ ID NO: 15)
GACATCGTGATGACCCAGTCTCC

IGKV5
                                    (SEQ ID NO: 16)
GAAACGACACTCACGCAGTCTC

IGKV6
                                    (SEQ ID NO: 17)
GAWRTTGTGMTGACWCAGTCTC

IGLV1
                                    (SEQ ID NO: 18)
CAGTCTGTGYTGACKCAGCCRCCCTC

IGLV2
                                    (SEQ ID NO: 19)
CAGTCTGCCCTGACTCAGCCT

IGLV3
                                    (SEQ ID NO: 20)
TCCTATGAGCTGACWCAGSHVCCCKC

IGLV4
                                    (SEQ ID NO: 21)
CAGCCTGTGCTGACTCARTCVCCCTC

IGLV5
                                    (SEQ ID NO: 22)
CAGCCTGTGCTGACTCAGCCAACTTC

IGLV6
                                    (SEQ ID NO: 23)
AATTTTATGCTGACTCAGCCCCAC

IGLV7
                                    (SEQ ID NO: 24)
CAGGCTGTGGTGACTCAGGAGCCC

IGLV8
                                    (SEQ ID NO: 25)
CAGACTGTGGTGACCCAGGAGCC

IGLV9
                                    (SEQ ID NO: 26)
CAGCCTGTGCTGACTCAGCCACC

HC301.5constant
                                    (SEQ ID NO: 27)
GCAGCCCAGGGCSGCTGTGC Kappa102constant
                                    (SEQ ID NO: 28)
GCACACAACAGAGGCAGTTCCAG Lambda202constant
                                    (SEQ ID NO: 29)
CTTGRAGCTCCTCAGAGGAG
```

Heavy chain and light chain PCR amplification reactions were each divided into two reactions as follows: heavy chain families VH.1,2,3 (primers IGVH1a, IGVH1b, IGVH2, IGVH3) and VH.4,5,6,7 (primers IGVH4, IGVH5, IGVH6, and IGVH7); kappa chain families VK.1,2,3 (primers IGKV1, IGKV2, and IGKV3) and VK.4,5,6 (primers IGKV4, IGKV5, and IGKV6); and lambda chain families VL.1,2,3,4,5 (IGLV1, IGLV2, IGLV3, IGLV4, and IGLV5) and VL.6,7,8,9 (primers IGLV6, IGLV7, IGLV8, and IGLV9). A touchdown PCR amplification protocol was used for temperature cycling.

Following the reaction, PCR amplification products were treated with Exonucleasel (Exo) and Shrimp Alkaline Phosphatase (SAP) to remove excess nucleotides and primers from each of the PCR amplification reactions (U.S. Biologicals, Marblehead, Mass.). Initial PCR amplification products were directly sequenced to determine the variable sequences of both the heavy chains and light chains using Sanger sequencing. Second nested PCR amplifications were performed using germline-matched heavy chain and light chain variable oligonucleotides in order to insert a mammalian signal and constant region cloning sequences using the following oligonucleotide primers.

```
sVH1a:
                                    (SEQ ID NO: 30)
CCACCATGGGATGGTCATGTATCATCCTTTTTCTAGTA

GCAACTGCAACTGGAGTACATTCACAGG sVH2:
                                    (SEQ ID NO: 31)
CCACCATGGGATGGTCATGTATCATCCTTTTTCTAGTA

GCAACTGCAACTGGAGTACATTCACAGATCACCT sVH3vv:
                                    (SEQ ID NO: 32)
CCACCATGGGATGGTCATGTATCATCCTTTTTCTAGTA

GCAACTGCAACTGGAGTACATTCACAG sVH3g1:
                                    (SEQ ID NO: 33)
CCACCATGGGATGGTCATGTATCATCCTTTTTCTAGTA

GCAACTGCAACTGGAGTACATTCAGAGG sVH4:
                                    (SEQ ID NO: 34)
CCACCATGGGATGGTCATGTATCATCCTTTTTCTAGTA

GCAACTGCAACTGGAGTACATTCACAGGTGCAGCTGCA

GG sVH5:
                                    (SEQ ID NO: 35)
CCACCATGGGATGGTCATGTATCATCCTTTTTCTAGTA

GCAACTGCAACTGGAGTACATTCAGAGGTGCA sVH6:
                                    (SEQ ID NO: 36)
CCACCATGGGATGGTCATGTATCATCCTTTTTCTAGTA

GCAACTGCAACTGGAGTACATTCACAGGTACAGC sVH7:
                                    (SEQ ID NO: 37)
CCACCATGGGATGGTCATGTATCATCCTTTTTCTAGTA

GCAACTGCAACTGGAGTACATTCACAGGTGCA sVK1:
                                    (SEQ ID NO: 38)
CCACCATGGGATGGTCATGTATCATCCTTTTTCTAGTA

GCAACTGCAACTGGAGTACATTCAGACATCCAGATGAC

CCAGTCTCCATCCTCCCTG sVK2:
                                    (SEQ ID NO: 39)
CCACCATGGGATGGTCATGTATCATCCTTTTTCTAGTA

GCAACTGCAACTGGAGTACATTCAGATATTGTGATGAC

TCAGTCTCACTCTCCCTGC sVK3:
                                    (SEQ ID NO: 40)
CCACCATGGGATGGTCATGTATCATCCTTTTTCTAGTA

GCAACTGCAACTGGAGTACATTCAGAAATTGTGTTGAC

ACAGTCTCCAGCCACCCTGTCTTTG sVK4:
                                    (SEQ ID NO: 41)
CCACCATGGGATGGTCATGTATCATCCTTTTTCTAGTA

GCAACTGCAACTGGAGTACATTCAGACATCGTGATGAC

CCAGTCTCCAGACTCCCTGGCTGTG sVK5:
                                    (SEQ ID NO: 42)
CCACCATGGGATGGTCATGTATCATCCTTTTTCTAGTA

GCAACTGCAACTGGAGTACATTCAGAAACGACACTCAC

GCAGTCTCCAGC sVK6:
                                    (SEQ ID NO: 43)
CCACCATGGGATGGTCATGTATCATCCTTTTTCTAGTA

GCAACTGCAACTGGAGTACATTCAGAAATTGTGCTGAC

TCAGTCTCCAGACTTTCG sVL1:
                                    (SEQ ID NO: 44)
CCACCATGGGATGGTCATGTATCATCCTTTTTCTAGTA

GCAACTGCAACTGGAGTACATTCACAGTCTGTGYTGAC

KCAGCCRCCCTC sVL2:
                                    (SEQ ID NO: 45)
CCACCATGGGATGGTCATGTATCATCCTTTTTCTAGTA

GCAACTGCAACTGGAGTACATTCACAGTCTGCCCTGAC

TCAGCCT sVL3:
                                    (SEQ ID NO: 46)
CCACCATGGGATGGTCATGTATCATCCTTTTTCTAGTA

GCAACTGCAACTGGAGTACATTCATCCTATGAGCTGAC

WCAGSHVCCCKC sVL4:
                                    (SEQ ID NO: 47)
CCACCATGGGATGGTCATGTATCATCCTTTTTCTAGTA

GCAACTGCAACTGGAGTACATTCACAGCCTGTGCTGAC

TCARTCVCCCTC sVL5:
                                    (SEQ ID NO: 48)
CCACCATGGGATGGTCATGTATCATCCTTTTTCTAGTA

GCAACTGCAACTGGAGTACATTCACAGCCTGTGCTGAC

TCAGCCAACTTC sVL6:
                                    (SEQ ID NO: 49)
CCACCATGGGATGGTCATGTATCATCCTTTTTCTAGTA

GCAACTGCAACTGGAGTACATTCAAATTTTATGCTGAC

TCAGCCCCAC
```

```
sVL7:
                                         (SEQ ID NO: 50)
CCACCATGGGATGGTCATGTATCATCCTTTTTCTAGTA

GCAACTGCAACTGGAGTACATTCACAGGCTGTGGTGAC

TCAGGAGCCC sVL8:
                                         (SEQ ID NO: 51)
CCACCATGGGATGGTCATGTATCATCCTTTTTCTAGTA

GCAACTGCAACTGGAGTACATTCACAGACTGTGGTGAC

CCAGGAGCC wVL9:
                                         (SEQ ID NO: 52)
CCACCATGGGATGGTCATGTATCATCCTTTTTCTAGTA

GCAACTGCAACTGGAGTACATTCACAGCCTGTGCTGAC

TCAGCCACC

Heavy constant:
                                         (SEQ ID NO: 53)
GCCAGGGGGAAGACCGATG Kappa constant:
                                         (SEQ ID NO: 54)
CTGGGATAGAAGTTATTCAGCAGGCACACAACAGAAGC

AGTTCCAGATTTCAACTGCTC

Lambda constant:
                                         (SEQ ID NO: 55)
CTTGRAGCTCCTCAGAGGAG
```

PCR amplification reactions were set up using PrimeStar HS DNA Polymerase with GC (Takara Bio, Shiga, Japan) according to the manufacturer's recommendation. Following the PCR amplification reactions, the amplification products were treated with Exo/SAP as described above. Heavy variable chain and light variable chain encoding PCR amplification products were inserted into a mammalian expression vector using restriction endonuclease free procedures. 20 µl of the PCR amplification products were annealed onto single stranded DNA human templates for $IgG_1$, kappa, and lambda chain using the Kunkel mutagenesis protocol. (See Kunkel (1985) PNAS 82:488-492.) Correctly inserted constructs were confirmed by DNA sequencing. Plasmids containing nucleic acids encoding heavy chains and light chains were co-transfected into 293T human embryonic kidney cells using Fugene transfection reagent (Roche Diagnostic, Indianapolis, Ind.) for transient expression, and analyzed for expression and binding as described below in Example 4.

Example 4

H7 Hemagglutinin ELISA Screening Assay

The ability of anti-influenza mAb1, anti-influenza mAb2, and anti-influenza mAb3 to bind H7 HA, the following studies were performed.

Nucleic acid encoding H7 HA from A/Shanghai/1/2013 (FIG. 7; SEQ ID NO:86)) and from A/Anhui/1/2013 (FIG. 8; SEQ ID NO:87) were synthesized by Blue Heron Biotech, An OriGene Company from Bothell, Wash. Nucleic acid encoding the H7 HA protein were subcloned into the mammalian expression vector pRK.sm (Genentech Inc) prior to transfection and expression. The H7 HA proteins were expressed as full-length proteins on the surface of 293T cells, prior to enzyme-linked immunosorbent assay detection.

To generate full-length HA lysates, 293T cells in 10 cm culture dishes (Corning Cat#430167) were transfected with H7 HA-expressing plasmids using a calcium phosphate method. 48 hours later, cells were treated with 1 mL lysis buffer (50 mM Tris, pH 8, 5 mM EDTA pH 8, 150 mM NaCl, 1% Triton X-100 (EMD, Cat#9410), plus Protease Inhibitor Cocktail Tablet (Roche, Cat#11836153001) for 20 minutes at room temperature. Lysates were centrifuged at 14,000 rpm for 10 minutes. Supernatants were stored at −80° C. and used in ELISA studies.

For ELISA studies, Nunc Maxisorp 96-well plates (Cat #439454) were coated with 5 ug/ml *Galanthus nivalis* lectin (Sigma Cat#L-8275) in PBS for 6 hours at room temperature. The plates were then washed with Washing Buffer (PBS, pH 7.4, +0.05% Tween-20 (EMD, Cat#1296)) and incubated in Blocking Buffer (PBS, pH 7.4, +0.5% BSA (bovine serum albumin, Gibco Cat#15260)) for 1 hour at room temperature. The plates were then washed and incubated with 293T cell lysates (1:300) in Assay Diluent (PBS, pH 7.4, +0.5% BSA+0.05% Tween-20) overnight at 4° C. The plates were then washed and incubated with serially diluted antibodies in Assay Diluent for 1.5 hours at room temperature.

After a subsequent wash step, the plates were incubated with goat-anti-human-IgG-HRP (Jackson ImmunoResearch, Cat#109-036-098) at 1:30000 or goat-anti-mouse-IgG-HRP (Jackson ImmunoResearch, Cat#115-035-071) at 1:20000 in Assay Diluent for 1 hour at room temperature. Plates were washed and incubated with the TMB Substrate (KPL, Cat#50-65-00) for 5-10 minutes at room temperature; 1M phosphoric acid was then added to stop the reaction. Absorbance at 450 nM was measured on a BioTek Synergy2 plate reader with the Gen5 software. Data analysis and graphing of the antibody binding to H7 HA was generated with the Prism software.

Figure 1B:
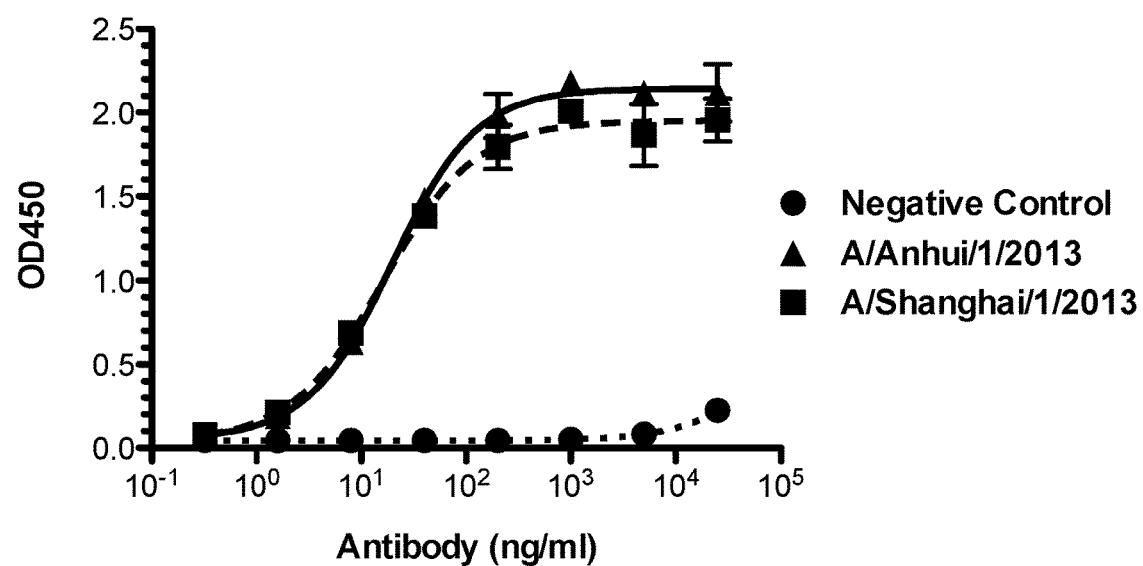
Figure 1C:
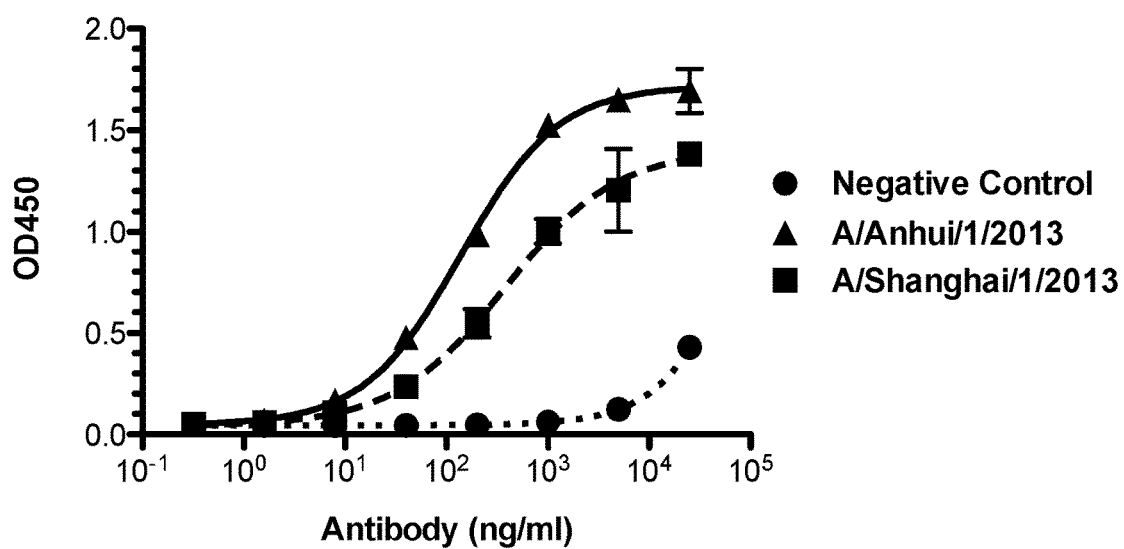

ELISA assays were performed for all three antibodies to test binding to the H7 HA proteins from A/Shanghai/1/2013 and A/Anhui/1/2013. As a negative control all three antibodies were tested for binding by ELISA to a lysate that did not contain H7 HA protein. Anti-influenza mAb1 (FIG. 1A), anti-influenza mAb2 (FIG. 1B), and anti-influenza mAb3 (FIG. 1C) exhibited specific binding to both H7 HA proteins tested. Very minimal binding activity to the negative control lysate was observed for all three antibodies, even at the highest antibody concentration tested (25,000 ng/ml). (See FIGS. 1A, 1B, and 1C.) The ELISA binding data were fit with a sigmoidal dose-response curve to calculate the binding $IC_{50}$ value and 95% confidence interval for each antibody. (See Table 2 below.)

TABLE 2

| Anti-influenza A antibody | A/Anhui/1/2103 H7 HA | | A/Shanghai/1/2013 H7 HA | |
|---|---|---|---|---|
| | $EC_{50}$ ng/ml | 95% CI ng/ml | $EC_{50}$ ng/ml | 95% CI ng/ml |
| mAb1 | 20 | 13-31 | 38 | 18-83 |
| mAb2 | 20 | 15-27 | 16 | 10-26 |
| mAb3 | 138 | 110-174 | 379 | 198-726 |

These results showed that all three of the antibodies tested in this assay can bind specifically to H7 HA proteins from A/Shanghai/1/2013 and A/Anhui/1/2013, two of the first human influenza A H7N9 virus strains isolated during the 2013 avian influenza A H7N9 virus outbreak in China.

Example 5

In Vitro Neutralization of Influenza a 117N9 Virus

The ability of the anti-influenza A H7N9 virus antibodies of the present invention to neutralize influenza A H7N9 virus in vitro was examined as follows.

In vitro neutralization studies were carried out within a BSL3 facility at Virapur LLC, San Diego, Calif. The influenza A H7N9 virus strain A/Shanghai/2/2013 IDCDC RG32A was used in the in vitro neutralization studies. To test neutralization, approximately 100 infectious units of virus were mixed with each antibody at concentrations ranging from 200 to 1.56 µg/ml and allowed to incubate for 1 hour. The virus/antibody mixtures were then placed onto a confluent monolayer of MDCK cells that were cultured in flat bottom clear 96-well plates. Each antibody concentration was tested in triplicate. The virus in the presence of antibody was allowed to infect the MDCK cells for 68 to 72 hours at 37° C. After infection, the antibody virus solution was removed and the MDCK cells were fixed and stained with crystal violet to visualize infected and non-infected MDCK monolayers. Wells that contained intact non-infected monolayers of MDCK cells stain dark blue with crystal violet; wells that exhibit infected MDCK monolayers do not stain dark blue with crystal violet.

Figure 2A:
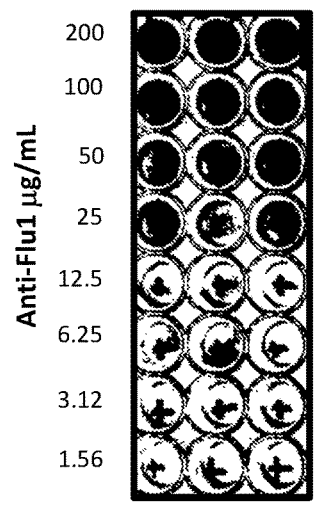
FIGS. 2A, 2B, and 2C set forth data showing in vitro neutralization of influenza A H7N9 virus strain A/Shanghai/2/2013 IDCDC RG32A by mAb1, mAb2, and negative control antibody, respectively.
Figure 2B:
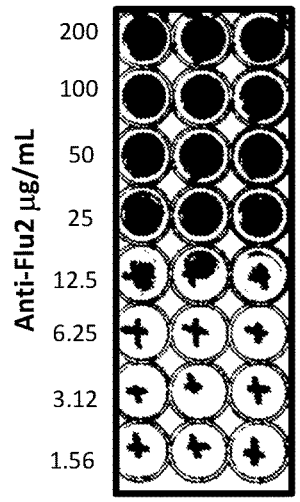

Anti-influenza A virus mAb1 and anti-influenza A virus mAb2, which showed the most potent H7 HA binding capacity, were able to completely block influenza A H7N9 viral infection at antibody concentrations of 200 to 25 µg/ml (FIGS. 2A and 2B). An anti-hemagglutinin antibody (mAb 81.39 containing a Trp residue in place of a Tyr residue at position 6 in HVR-L3), previously shown to be effective at neutralizing Grp2 influenza A virus (see U.S. patent application Ser. No. 14/077,414, which is incorporated by reference herein in its entirety) was not effective at neutralizing influenza A H7N9 virus in this assay (data not shown), indicating that the anti-influenza A H7N9 virus antibodies of the present invention have the unexpected benefit of effectively neutralizing influenza A H7N9 virus.

Figure 2C:
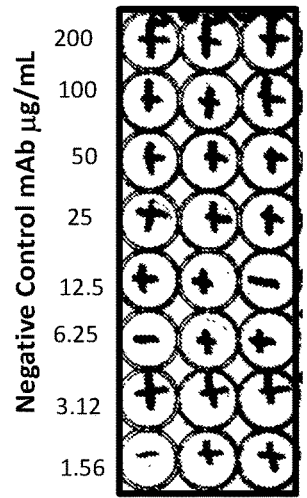

As a negative control, an antibody that does not bind to H7 HA was also tested for the ability to block influenza A H7N9 virus infectivity. This negative control antibody showed no in vitro neutralization ability even at the highest antibody concentration tested (200 µg/ml) (FIG. 2C). The minimum inhibitory concentration values (MIC) for mAb1 (anti-Flu1) and mAb2 (anti-Flu2) in this assay were 25 µg/ml, while an MIC for the negative control antibody could not be determined (Table 3).

TABLE 3

| Antibody | A/Shanghai/2/2013 IDCDC RG32A (MIC µg/ml) |
|---|---|
| mAb1 | 25 |
| mAb2 | 25 |
| Negative control | No inhibition |

These results showed that monoclonal antibodies of the present invention were able to neutralize in a dose-dependent manner influenza A H7N9 virus in vitro. These results indicated that antibodies of the present invention are effective in the treatment and prevention of influenza A H7N9 virus infection.

Example 6

In Vivo Efficacy of Anti-Influenza a 117N9 Virus Antibody in Mice and Ferrets Mice and ferret influenza A virus infection models are often used to examine prophylactic and therapeutic efficacy of anti-influenza therapeutics. Ferrets are considered a clinically relevant animal model for human influenza A virus infection. (See Matsuoka et al., (2009) *Current Protocols in Microbiology*, Chapter 15, Unit 15G 12.)

The in vivo efficacy anti-influenza A H7N9 virus antibodies in mice and ferrets is performed as follows. DBA/2J mice (Jackson Lab, Bar Harbor, Me.) or male ferrets (*Mustela putorius furo*) are infected intranasally with 50 µl of various influenza A H7N9 virus clades diluted in influenza media (DMEM, 0.2% BSA, 2 µg/mL TPCK-treated trypsin) at the minimum $LD_{100}$ dose. Influenza virus infection is allowed to progress for 24-72 hours prior to the intravenous administration of antibody.

After 72 hours post influenza A H7N9 virus infection, various amounts of antibody are administered intravenously to the mice and ferrets at various doses (e.g., 45 mg/kg, 15 mg/kg, 5 mg/kg, 1.5 mg/kg, and 0.6 mg/kg) in 200 µl PBS. Mice and ferrets are monitored daily for body conditioning and survival, and also weighed daily, until 21 days after infection.

Percent survival (over time, in days) of mice and ferrets administered various amounts of antibody at 24, 48, and 72 hours after infection with influenza A H7N9 virus is determined. The results show that monoclonal antibodies of the present invention are effective at treating various influenza A H7N9 virus infections. Additionally, these data show that monoclonal antibodies of the present invention are effective at treating influenza A H7N9 virus infection when administered up to at least 72 hours post influenza A H7N9 virus infection.

Example 7

In Vivo Efficacy of Anti-Influenza a 117N9 Antibody and Oseltamivir in Mice and Ferrets To compare the efficacy of anti-influenza A H7N9 antibodies to that of oseltamivir phosphate (Tamiflu®) in mice and ferrets, the following studies are performed. Balb/c mice (Charles River Laboratories, Hollister, Calif.) at 6-weeks old are infected intranasally with 50 µl influenza A H7N9 virus at 100× the lethal dose. Male ferrets (*Mustela putorius furo*) are challenged with an intranasal dose of influenza A H7N9 virus at, for example, $1 \times 10^3$ pfu. At 48 hours post infection, anti-influenza A H7N9 antibodies are administered as a single dose (e.g., approximately 45 mg/kg, 15 mg/kg, 5 mg/kg, 1.5 mg/kg, or 0.6 mg/kg) or control IgG in 200 µl PBS intravenously. In these experiments, an oseltamivir dosing regimen consisting of 2 mg dosed twice daily (BID) for five days are compared with a single dosing regimen of anti-influenza A H7N9 virus antibody.

Percent mortality in each treatment group is determined. The results show that anti-influenza A H7N9 antibodies of the present invention are more effective at treating influenza A H7N9 virus infection in mice and in ferrets compared to that of oseltamivir.

Example 8

In Vivo Efficacy of Anti-Influenza a 117N9 Virus Antibody in Mice and Ferrets with and without Co-Administration of Oseltamivir Administration of oseltamivir is effective at reducing human influenza A virus infection if given within 48 hours after symptom onset. Unfortunately, oseltamivir shows minimal efficacy in patients who have been symptomatic for more than 48 hours. Therefore, the following experiments are performed to test if co-administration of an anti-influenza A H7N9 virus antibody and oseltamivir show improved efficacy over either treatment alone. These experiments are performed using a mouse or ferret influenza infection model, such as that described above in Example 7. Briefly, female Balb/C mice (Charles River Laboratories) are infected with 100× the lethal dose of influenza A H7N9 virus, and male ferrets (*Mustela putorius furo*) are challenged with an intranasal dose of influenza A H7N9 virus at, for example, $1 \times 10^3$ pfu 72-hours prior to i.v. administration of a single sub-efficacious does of anti-influenza A H7N9 antibody, control IgG, 2 mg BID oseltamivir, or a combination of a single dose of anti-influenza A H7N9 antibody and oseltamivir treatment for 5 days.

Percent mortality in each treatment group is determined. A comparison is made to determine if a synergistic effect occurred during combination therapy using an anti-influenza A H7N9 virus antibody used in combination with oseltamivir, a neuraminidase inhibitor.

These results showed that broadly neutralizing anti-hemagglutinin antibodies of the present invention were highly protective in the treatment of influenza A H7N9 virus infection in ferrets and performed better than oseltamivir when administered at 24, 48, and 72 hours post influenza A H7N9 virus infection.

Example 9

Prophylactic Treatment

Antibodies of the present invention are useful in the prophylactic treatment of influenza A H7N9 virus infection. Such treatment provides prophylactic therapy to individuals at risk for exposure to or infection of influenza A H7N9 virus. The anti-influenza A H7N9 virus antibodies are tested in prophylactic in vivo animal models to establish their ability to provide prophylactic treatment in response to an influenza A H7N9 virus outbreak in humans. Several in vivo H7N9 animal models are available in mice and ferrets with a range of clinical outcomes from mild disease to mortality. Intravenous delivery of these antibodies at concentration between 5 to 50 mg/ml to these animals prior to infection is used to assess their prophylactic activity to mitigate infection and severe disease associated with influenza A H7N9 virus.

Statistical Analyses

Statistics were calculated using JMP version 9.0.2 software (SAS Institute). Survival experiments were compared using log-rank test. P values<0.05 were considered significant. $IC_{50}$ curves and values were plotted and calculated using Graphpad Prism version 5.0 software.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

What is claimed is:

1. A method for preventing or treating influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
   (a) HVR-H1 comprises the amino acid sequence of SEQ ID NO:56;
   (b) HVR-H2 comprises the amino acid sequence of SEQ ID NO:57;
   (c) HVR-H3 comprises the amino acid sequence of SEQ ID NO:58;
   (d) HVR-L1 comprises the amino acid sequence of SEQ ID NO:59;
   (e) HVR-L2 comprises the amino acid sequence of SEQ ID NO:60; and
   (f) HVR-L3 comprises the amino acid sequence of SEQ ID NO:61.

2. The method of claim 1, wherein the antibody comprises a heavy chain variable region comprising the amino acid sequence of SEQ ID NO:74.

3. The method of claim 1, wherein the antibody comprises a light chain variable region comprising the amino acid sequence of SEQ ID NO:75.

4. The method of claim 1, wherein the antibody comprises a heavy chain variable region and a light chain variable region, wherein the heavy chain variable region comprises the amino acid sequence of SEQ ID NO:74, and the light chain variable region comprises the amino acid sequence of SEQ ID NO:75.

5. The method of claim 1, wherein the antibody comprises a heavy chain comprising the amino acid sequence of SEQ ID NO:76.

6. The method of claim 1, wherein the antibody comprises a light chain comprising the amino acid sequence of SEQ ID NO:77.

7. The method of claim 1, wherein the antibody comprises a heavy chain and a light chain, wherein the heavy chain comprises the amino acid sequence of SEQ ID NO:76, and the light chain comprises the amino acid sequence of SEQ ID NO:77.

8. A method for preventing or treating influenza A H7N9 virus infection, the method comprising administering to a subject having or at risk for having influenza A H7N9 virus infection a therapeutically effective amount of an antibody, wherein the antibody comprises three heavy chain hypervariable regions (HVR-H1, HVR-H2, and HVR-H3) and three light chain hypervariable regions (HVR-L1, HVR-L2, and HVR-L3), wherein:
- (a) HVR-H1 comprises the amino acid sequence of SEQ ID NO:62;
- (b) HVR-H2 comprises the amino acid sequence of SEQ ID NO:63;
- (c) HVR-H3 comprises the amino acid sequence of SEQ ID NO:64;
- (d) HVR-L1 comprises the amino acid sequence of SEQ ID NO:65;
- (e) HVR-L2 comprises the amino acid sequence of SEQ ID NO:66; and
- (f) HVR-L3 comprises the amino acid sequence of SEQ ID NO:67.

9. The method of claim 8, wherein the antibody comprises a heavy chain variable region comprising the amino acid sequence of SEQ ID NO:78.

10. The method of claim 8, wherein the antibody comprises a light chain variable region comprising the amino acid sequence of SEQ ID NO:79.

11. The method of claim 8, wherein the antibody comprises a heavy chain variable region and a light chain variable region, wherein the heavy chain variable region comprises the amino acid sequence of SEQ ID NO:78, and the light chain variable region comprises the amino acid sequence of SEQ ID NO:79.

12. The method of claim 8, wherein the antibody comprises a heavy chain comprising the amino acid sequence of SEQ ID NO:80.

13. The method of claim 8, wherein the antibody comprises a light chain comprising the amino acid sequence of SEQ ID NO:81.

14. The method of claim 8, wherein the antibody comprises a heavy chain and a light chain, wherein the heavy chain comprises the amino acid sequence of SEQ ID NO:80, and the light chain comprises the amino acid sequence of SEQ ID NO:81.

15. The method of any one of claims 1-14, wherein the method further comprises administering an additional therapeutic agent, wherein the additional therapeutic agent is a neuraminidase inhibitor, an anti-hemagglutinin antibody, or an anti-M2 antibody.

16. The method of claim 15, wherein the neuraminidase inhibitor is oseltamivir, zanamivir, or peramivir.

* * * * *